(12) United States Patent
Meyer et al.

(10) Patent No.: US 8,551,719 B1
(45) Date of Patent: Oct. 8, 2013

(54) ENDOTOXIN DETECTION METHOD

(71) Applicant: Hyglos Invest GmbH, Bernried (DE)

(72) Inventors: Roman Meyer, Schmidmuhlen (DE); Michael Schütz, Kareth-Lappersdorf (DE); Holger Grallert, Schriesheim (DE); Renate Grassl, Regensburg (DE); Stefan Miller, Regensburg (DE)

(73) Assignee: Hyglos Invest GmbH, Bernried (DE)

( * ) Notice: Subject to any disclaimer, the term of this patent is extended or adjusted under 35 U.S.C. 154(b) by 0 days.

(21) Appl. No.: 13/772,117

(22) Filed: Feb. 20, 2013

Related U.S. Application Data

(63) Continuation of application No. 10/583,415, filed as application No. PCT/DE2004/002778 on Dec. 20, 2004, now Pat. No. 8,394,597.

(30) Foreign Application Priority Data

Dec. 20, 2003 (DE) .................................. 103 60 844

(51) Int. Cl.
*G01N 31/00* (2006.01)
*G01N 33/53* (2006.01)

(52) U.S. Cl.
USPC ........... 435/7.21; 435/7.1; 436/501; 436/518; 424/130.1; 424/9.1; 422/430; 530/300; 530/350

(58) Field of Classification Search
None
See application file for complete search history.

(56) References Cited

U.S. PATENT DOCUMENTS

| | | | |
|---|---|---|---|
| 4,906,567 | A | 3/1990 | Connelly |
| 6,436,653 | B1 | 8/2002 | Jakobsen et al. |
| 2004/0248298 | A1 | 12/2004 | Schutz et al. |
| 2006/0172281 | A1 | 8/2006 | Schutz et al. |

FOREIGN PATENT DOCUMENTS

| | | |
|---|---|---|
| DE | 10129815 | 1/2003 |
| DE | 10228133 | 1/2004 |
| DE | 10307793 | 9/2004 |
| WO | WO 03/000888 | 1/2003 |
| WO | WO 2004/001418 | 12/2003 |
| WO | WO 2005/062051 | 7/2005 |

OTHER PUBLICATIONS

Baxa et al., "Enthalpic Barriers to the Hydrophobic Binding of Oligosaccharides to Phase P22 Tailspike Protein," *Biochemistry*, 40:5144-5150, 2001.
Burda et al., "Stability of Bacteriophage T4 Short Tail Fiber," *Biol. Chem.*, 381:255-258, 2000.
Crowther, "Enzyme-linked immunosorbent assay (ELISA)," *Molecular Biomethods Handbook*, Chapter 46, pp. 595-617, 1998.
King and Laemmli, "Polypeptides of the tail fibres of bacteriphage T4," *J. Mol. Biol.*, 62:465-477, 1971.
Lee and Tsai, "Quantification of Bacterial Lipopolysaccharides by the Purpald Assay: Measuring Formaldehyde Generated from 2-keto-3-deoxyoctonate and Heptose at the Inner Core," *Analytical Biochemistry*, 267:161-168, 1999.
Lyngby et al., "Quantification of Lipopolysaccharides in Outer Membrance Vesicle Vaccines Against Meningococcal Disease, High-performance Liquid Chromatographic Determination of the Constituent 3-Hydroxy-lauric Acid," *Biologicals*, 30:7-13, 2002.
Office Action issued in Canadian Application No. 2,549,530, mailed Apr. 4, 2012.
Office Action issued in Canadian Application No. 2,549,530, mailed May 16, 2011.
Office Action issued in U.S. Appl. No. 10/583,415, mailed Nov. 10, 2011.
PCT International Preliminary Report on Patentability issued in International Application No. PCT/DE2004/002778, dated Jun. 20, 2006.
PCT International Search Report issued in International Application No. PCT/DE2004/002778, mailed Jun. 17, 2005.
Riede, "Receptor specificity of the short tail fibres (gp12) of T-even type *Escherichia coli* phages," *Mol. Gen. Genet.*, 206:110-115, 1987.
Skerra and Schmidt, "Applications of a Peptide Ligand for Streptavidin: The Strep-tag," *Biomolecular Engineering*, 16:79-86, 1999.
Sun et al., "Use of Bioluminescent *Salmonella* for Assessing the Efficiency of Constructed Phage-Based Biosorbent," *Journal of Industrial Microbiology & Biotechnology*, 25:273-275, 2000.
Suzuki et al., "Specific interaction of fused H protein of bacteriophage phiX174 with receptor lipopolysaccharides," *Virus Research*, 60:95-99, 1999.
Thomassen et al., The Structure of the Receptor-binding Domain of the Bacteriophage T4 Short Tail Fibre Reveals a Knitted Trimeric Metal-binding Fold, *J. Mol. Biol.*; 331:361-373, 2003.
Van Raaij et al., "Crystal structure of a heat and protease-stable part of the bacteriophage T4 short tail fibre," *J. Mol. Biol.*, 314:1137-1146, 2001.

*Primary Examiner* — Lisa Cook
(74) *Attorney, Agent, or Firm* — Parker Highlander PLLC

(57) ABSTRACT

The invention relates to a method for detecting endotoxins in a sample.

16 Claims, 8 Drawing Sheets

Fig. 3

| Endotoxin structure | E. coli strain | p-12 bond |
|---|---|---|
| KDO-LipidA / KDO / KDO | D21f2 | - |
| Hep-Hep-KDO-LipidA / Hep  KDO / KDO | D21f1 | + |
| Glc-Hep-Hep-KDO-LipidA / Hep  KDO / KDO | D21e8 | + |
| Glc-Hep-Hep-KDO-LipidA / Gal Hep  KDO / KDO | D21e7 | + |
| GlcN-Glc-Glc-Glc-Glc-Hep-Hep-KDO-LipidA / Gal Hep  KDO / KDO | D21 | + |

| pH | $K_d$ |
|---|---|
| 6.0 | 3.09 E-07 |
| 7.5 | 6.85 E-08 |
| 8.0 | 5.86 E-08 |
| 8.5 | 7.86 E-08 |
| 9.0 | 3.29 E-08 |
| 10.0 | 1.55 E-07 |

```
T2p12          MSNNTYQHVSNESRYVKFDPTDTNFPPEITDVQAAIAAISPAGVNGVPDASSTTKGILFL
K3p12          MSNNTYQHVSNESRYVKFDPTDTNFPPEITDVQAAIAAISPAGVNGVPDASSTTKGILFL
T4p12          MSNNTYQHVSNESRYVKFDPTDTNFPPEITDVHAAIAAISPAGVNGVPDASSTTKGILFI
RB32-33p12     MSNNTYQHVSNESKYVKFDPVGSNFPDTVTTVQSALSKISNIGVNGIPDATMEVKGIAMI
AR1p12         MSNNTYQHVSNESKYVKFDPTGSNFPDTVTTVQSALSKISNIGVNGIPDAEMEVKGIAMI
PP01p12        MSNNTYQHVSNESKYVKFDPVGSNFPDTVTTVQSALSKISNIGVNGIPDASMEVKGIAMI
RB69p12        MSNNTYQHVSNESVYVEFDPTGSNFDSSITNVQAALASISAYGVKGVPDASEAKGVIQL
               ************  *:*** : :**   :* *;:*;; **  **:*:***;   **:  :

T2p12          ATEQEVIDGTDNTKAVTPATLATRLSYPNATEAVYGLTRYSTDDEAIAGVNNESSITPAK
K3p12          ATEQEVIDGTDNTKAVTPATLATRLSYPNATETVYGLTRYSTNDEAIAGVNNESSITPAK
T4p12          PTEQEVIDGTDNTKAVTPATLATRLSYPNATETVYGLTRYSTNDEAIAGVNNESSITPAK
RB32-33p12     ASEQEVLDGTNNSKIVTPATLATRLLYPNATETKYGLTRYSTNEETLEGSDNNSSITPQK
AR1p12         ASEQEVLDGTNNSKIVTPATLATRLLYPNATETKYGLTRYSTNEETLEGSDNNSSITPQK
PP01p12        ASEQEVLDGTDISKIVTPATLATRLLYPNATETKYGLTRYSTNEETLEGSDNNSSITPQK
RB69p12        ATEQEVLDGFNSTKAVTPATLNARLQYPNASETQYGVTKYATQEEAIAGTIDTVSITPLK
               ..:****:**  *.:*  ****** :** ****:*;  **:*:*;*;:*::  *  .:  .****  *

T2p12          FTVALMNVFETRVSTESSNGVIKISSLPQALAGADDTTAMTPLKTQQLAVKLIAQIAPSK
K3p12          FTVALNNAFETRVSTESSNGVIKISSLPQALAGADDTTAMTPLKTQQLAIKLIAQIAPSE
T4p12          FTVALNNAFETRVSTESSNGVIKISSLPQALAGADDTTAMTPLKTQQLAIKLIAQIAPSE
RB32-33p12     LKYHTDDVFQNRYSSESSNGVIKISSTPAALAGVDDTTAMTPLKTQKLAIKLISQIAPSE
AR1p12         LKYHTDDVFQNRYSSESSNGVIKISSTPAALAGVDDTTAMTPLKTQKLAIKLISQIAPSE
PP01p12        LKYHTDDVFQNRYSSESSNGVIKISSTPAALAGVDDTTAMTPLKTQKLAIKLISQIAPSE
RB69p12        LNQTIDNTFSTRYSTETTNGVIKIATQTAALAGSDDTTAMTPLKTQQLAIKLISQIAPRN
               :.   :: .*..* *;*::****** ;    **** **********:**;***.*****.:

T2p12          NAATESEQGVIQLATVAQAFQGTLREGYAISPYTFMNSTATEEYKGVIKLGTQSEVNSIN
K3p12          TTATESDQGVVQLATVAQVRQGTLREGYAISPYTFMNSSATEEYKGVIKLGTQSEVNSNN
T4p12          TTATESDQGVVQLATVAQVRQGTLREGYAISPYTFMNSSSTEEYKGVIKLGTQSEVNSNN
RB32-33p12     DTASESVRGVVQLSTVAQTRQGTLREGYAISPYTFMNSVATQEYKGVIRLGTQSEINSNL
AR1p12         DTASESVRGVVQLSTVAQTRQGTLREGYAISPYTFMNSVATQEYKGVIRLGTQSEINSNL
PP01p12        DTASESVRGVVQLSTVAQTRQGTLREGYAISPYTFMNSVATQEYKGVIRLGTQSEINSNL
RB69p12        DPASESITGVVRLATVAQTRQGTLREGYAISPYTFMNSVATQEYKGVIRLGTQAEINSNL
                .*:**   **;;*;:**** **************  ;*;******;****;*;***

T2p12          ASVAVTGATLNGRGSTTSMRGVVKLTTTAGSQSGGDASSALAWNADVIHQRGGQTINGTL
K3p12          ASVAVTGATLNGRGSTTSMRGVVRLTTTAGSQSGGDASSALAWNADVIHQRGGQTINGTL
T4p12          ASVAVTGATLNGRGSTTSMRGVVKLTTTAGSQSGGDASSALAWNADVIQQRGGQIIYGTL
RB32-33p12     GDVAVTGETLNGRGATSSMRGVVKLTTQAGIAPEGDSSGALAWNADVINTPGGQTINGSL
AR1p12         GDVAVTGGTLNGRGATGSMPGVVKLTTQAGIAPEGDSSGALAWNADVINTRGGQTINGSL
PP01p12        GDVAVTGETLNGRGATGSMRGVVKLTTQAGIAPEGDSSGALAWNADVINTRGGQTINGSL
RB69p12        GDVAVTGETLNGRGATGSMRGVVKLTTQAGVAPEGDSSGALAWNADVINTRGGQTINGSL
               .,.*****  ******;* ****** ;*** **   ** *.**********;  **** * *;*

T2p12          RINNTLTIASGGANITGTVNMTGGYIQGEPVVTQNEIDRTIPVGAIMMWAADSLPSDAWR
K3p12          RINNTLTIASGGANITGTVNMTGGYIQGKRVVTQNEIDRTIPVGAIMMWAADSLPSDAWR
T4p12          RIEDTFTIANGGANITGTVRMTGGYIQGNRIVTQNEIDRTIPVGAIMMWAADSLPSDAWR
RB32-33p12     NLD---HLTANGIWSRGGMWKNG----DQPVATERYASERVPVGTIMMFAGDSAP-PGWI
AR1p12         NLD---HLTANGIWSRGGMWKNG----DQPVATERYASERVPVGTIMMFAGDSAP-PGWI
PP01p12        NLD---HLTANGIWSRGGMWKNG----DQPVATERYASERVPVGTIMMFAGDSAP-PGWI
RB69p12        NLD---HLTANGIWSRGGMWKNG----DQPVATERYASERVPVGTIQMFAGDSAP-PGWV
                .::  .  .*  .  .*    .*    ;; .: *;*. .. ***;.* *;**  *.*
```

Fig. 7B

```
T2p12        FCHGGTVSASDCPLYASPIGTRYGGTSSNPGLPDMRGLFVRGSGRGSHLTNPNVNGNDQF
K3p12        FCHGGTVSASDCPLYASRIGTRYGGSSSNPGLPDMRGLFVRGSGRGSHLTNPNVNGNDQF
T4p12        FCHGGTVSASDCPLYASRIGTRYGGNPSNPGLPDMRGLFVRGSGRGSHLTNPNVNGNDQF
RB32-33p12   MCHGGTVSGDQYPDYRNTVGARPGGDWNNPGIPDMRGLFVRGAGTGGHILNQ--RGQDGY
AR1p12       MCHGGTVSGDQYPDYRNTVGTRFGGDWNNPGIPDMRGLFVRGAGTGGHILNQ--RGQDGY
PP01p12      MCHGGTVSGDQYPDYRNTVGTRFGGDWNNPGIPDMRGLFVRGAGTGXHILNQ--RGQDGY
RB69p12      LCHGGTISGDQFPDYRNVVGTRFGGDWNNPGIPDMRGLFVRGAGTGGHILNN--RGQDGY
             :*****:*..: *  * .:*(*;** .***:***********:*  *:  *   .*;* :

T2p12        GKPRLGVGCTGGYVGEVQKQQMSYHKHAGGFGEY---DDSGAFGNTRRSNFVGTRKGLDW
K3p12        GKPRLGVGCTGGYVGEVQKQQMSYHKHAGGFGEW---DDSGAFGNTRRSNFVGTRKGLDW
T4p12        GKPRLGVGCTGGYVGEVQIQQMSYHKHAGGFGEH---DDLGAFGNTRRSNFVGTRKGLDW
RB32-33p12   GKDRLGVGCDGMHVGGVQAQQMSYHKHAGGNGEY--QRHEAPFGASVYQGYLGTRKYSDW
AR1p12       GKDRLGVGCDGMHVGGVQAQQMSYHKHAGGWGEY--NRSEGPFGASVYQGYLGTRKYSDW
PP01p12      GKDRLGVGCDGMHVGGVQAQQISYHKHAGANGENGNNRGYAPFGASNGSGYLGNGPSADW
RB69p12      GKDRLGVGCDGMHVGGVQAQQMSYHKHAGGWGEF--QRHEAPFGASVYQGYLGTRKYSDW
             ** ****** *  ;** ** **;*******;:**      ..** :   ...::*. :  **

T2p12        DNRSYFTNDGYEIDPASQRNSPYTLNRPELIGNETRPWNISLNYIIKVKE
K3p12        DNRSYFTNDGYEIDPASQRNSRYTLNRPELIGNETRPWNISLNYIIKVKE
T4p12        DNRSYFTNDGYEIDPESQRNSKYTLNRPELIGNETRPWNISLNYIIKVKE
RB32-33p12   DNASYFTNDGFELG--GPRDALGTLNREGLIGYETRPWNISLNYIIKIHY
AR1p12       DNASYFTNDGFELG--GPRDALGTLNREGLIGYETRPWNISLNYIIKIHY
PP01p12      DNHLPPTNDGPEMG--GPRDSPGTLNREGLIGYETRPWNISLNYIIKIHY
RB69p12      DNASYFTNDGFELG--GKRDATGTLNREGLIGYETRPWNISLNYIIKVHY
             ** ;*****:*;. .  *;;   **** *** ****;********::;
```

ENDOTOXIN DETECTION METHOD

CROSS-REFERENCE TO RELATED APPLICATIONS

This application is a continuation of U.S. application Ser. No. 10/583,415, filed as International Application No. PCT/DE2004/002778 on Dec. 20, 2004, which claims priority to German Application No. DE 103 60 844.3, filed Dec. 20, 2003. The entire text of each of the above-referenced disclosures is specifically incorporated herein by reference.

REFERENCE TO SEQUENCE LISTING

Pursuant to 37 C.F.R. 1.821(c), a sequence listing is submitted herewith as an ASCII compliant text file named "DEBEP0067USC1.txt", created on Feb. 19, 2013 and having a size of ~38 KB. The content of the aforementioned file is hereby incorporated by reference in its entirety.

BACKGROUND OF THE INVENTION

The present invention relates to methods for detecting endotoxins in a sample.

Endotoxin (ET) describes a family of lipopolysaccharides which together with proteins and phospholipids form the outer cell wall of Gram-negative bacteria. Endotoxins occur exclusively in this bacterial group and play an important role in the organisation, stability and barrier function of the outer membrane. Numerous bacteriophages use endotoxin or general lipopolysaccharide for specific detection of their host bacteria.

All endotoxin variants comprise a heteropolysaccharide which is bonded covalently to lipid A. Lipid A anchors endotoxin in the outer bacterial membrane. The heteropolysaccharide, which comprises a core oligosaccharide and the O antigen, appears in the surrounding solution and determines the serological identity of the bacterium. The O antigen comprises repetitive oligosaccharide units, the composition of which is strain-specific. Characteristic building blocks of the core oligosaccharide are 2-keto-3-deoxyoctonate (KDO) and L-glycero-D-mannoheptose (Hep).

The most conservative part of endotoxin of different types is the lipid A. The inner core region is preserved similarly to lipid A, the outer core region already has a higher variation. The inner core region, KDO and lipid A itself carry a plurality of phosphate groups as substituents and are therefore responsible for the negative charge of endotoxin. Furthermore, the phosphate groups on the lipid A and on the core region can be substituted variably with arabinose, ethanolamine and phosphate. Individual saccharide building blocks of the O antigen are acetylated, sialated or glycosylated. The O antigen varies in addition with respect to the number of repetitive units, for which reason the endotoxin population of each bacterium has a certain heterogeneity.

Endotoxins are biomolecules which can be found in practically all aqueous solutions without corresponding precautionary measures. Endotoxins in humans and animals can lead to sepsis, to a strong incorrect response of the immune system. Hence, for example when producing pharmaproteins, contamination with endotoxin should be detected precisely and should be removed completely subsequently. Endotoxin represents a problem with genetically engineered pharmaceuticals, gene therapeutics or substances, which are injected into humans or animals (e.g. veterinary treatment or in animal tests). However, not only in medicinal but also in research applications, such as transfection experiments of mammal cells, inhibition or lowering of the transfection efficiency by means of endotoxin can be observed.

In order to be able to use proteins within the framework of clinical studies, the European and American pharmacopoeia demand that the proteins fall below specific boundary values for endotoxin level (e.g. immune serum globulin 0.91 EU/ml, this corresponds to 5 EU/kg bodyweight and hour (dosage=EU/kg*h); EU=endotoxin unit; FDA (Food and Drug Administration): Guideline on Validation of LAL as End Product). If a medicine or proteins contained therein have too high an endotoxin level, this can lead to the death of the experimentee. The misdirected immune defence damages the patient due to overreaction. This can lead to tissue inflammation, drop in blood pressure, heart racing, thrombosis, shock etc. Even a longer enduring endotoxin exposition in picogram quantities can lead to chronic side effects, such as e.g. immune deficiencies, septic symptoms etc. Within the framework of substance production, in particular in processes with "good manufacturing practice" (GMP) conditions, it is therefore attempted to deplete endotoxin as far as possible. However, endotoxin removal in proteins, polysaccharides and DNA is problematic. In the case of proteins themselves, there are large problems due to their intrinsic properties, such as charge state or hydrophobicity, which can virtually prevent endotoxin removal or can lead to large product losses in the removal procedure.

At present, four methods for endotoxin detection in biological solutions are described, only the first two methods being permitted by the FDA. 1. "Rabbit Pyrogen Testing"; a method in which a living rabbit is injected with an endotoxin solution and hence an immune reaction is triggered. This endotoxin-induced immune response is detected by the development of fever. 2. The "*Limulus* Amoebocyte Lysate (LAL)"-Test, the test which is used most frequently at present (Bio Whittacker, Inc., Charles-River, Inc., Associates of Cape Cod, Inc., all USA), can be standardised in a significantly improved way. With this method, the agglomeration of the blood of the horseshoe crab (*Limulus polyphemus*) is measured after endotoxin contact. 3. The in vitro pyrogen test is based on the detection of interleukin-1β in human blood, which is involved in fever induction. The test consists of an incubation step of human blood with the solution to be examined, and the subsequent detection of the interleukin via antibodies. 4. A further possibility is the use of a special cell culture system (Sterogene Inc., USA) with which activation of monocytes is tracked via the appearance of specific cytokines.

The two first-mentioned methods are however very expensive and, due to the large requirement for test animals or for blood of the very rare horseshoe crab, are dubious not least on the grounds of animal protection. The LAL test can in fact also be miniaturised and automated but, due to low stability of the components, has huge disadvantages in application. Once a LAL solution has been opened it must be processed and used up immediately since the components aggregate within a few hours. The in vitro pyrogen test requires preferably fresh human blood and is relatively time consuming, as the production of the interleukin requires about 10 to 24 hours. Aside of endotoxins, other pyrogens may also be recognized with the pyrogen test. However, first of all, this test is used as substitute for the "rabbit pyrogen test". Skilled personnel are required for all test methods and the methods are very susceptible to interference, because for example the immune system of rabbits can react entirely differently to the same dose of endotoxin. The cell culture method of the Sterogene Company, like all cell culture methods, is likewise very complex and has problems with respect to standardisation.

It can be established overall that there is no easily handled economical method for endotoxin detection and the methods used at present have a series of disadvantages. There is therefore a requirement for a method which avoids these disadvantages.

BRIEF SUMMARY OF THE INVENTION

The object underlying the invention is therefore to provide a method which can detect endotoxins in solutions and samples faster, easier and more standardized.

The objects are achieved by the subject defined in the patent claims.

BRIEF DESCRIPTION OF THE DRAWINGS

The subsequent Figures explain the invention.

FIG. 3 shows schematically the structure of the endotoxin core region of various E. coli mutants.

FIGS. 7 A and B show a comparison of different p12 bacteriophage tail proteins on the amino acid level. The proteins are derived from phages of the myoviridae family and have a homology of at least 60% to T4p12. The p12 proteins used for the comparison are derived from phage T2 (NCBI data bank accession no: CAA39905; SEQ ID NO:9), T4 (AAD42417; SEQ ID NO:10), PP01 (BAD20635; SEQ ID NO:11), RB69 (AAP76072; SEQ ID NO:12) and AR1 (AAN03609; SEQ ID NO:13). Proteins of the phage K3 (Burda M. R. et al., Biol. Chem. (2000) 381, 225-258; SEQ ID NO: 14), RB32-33 (SEQ ID NO: 15) and ox 2 exhibit a similar homology to the above mentioned phages.

DETAILED DESCRIPTION OF THE INVENTION

Figure 1:
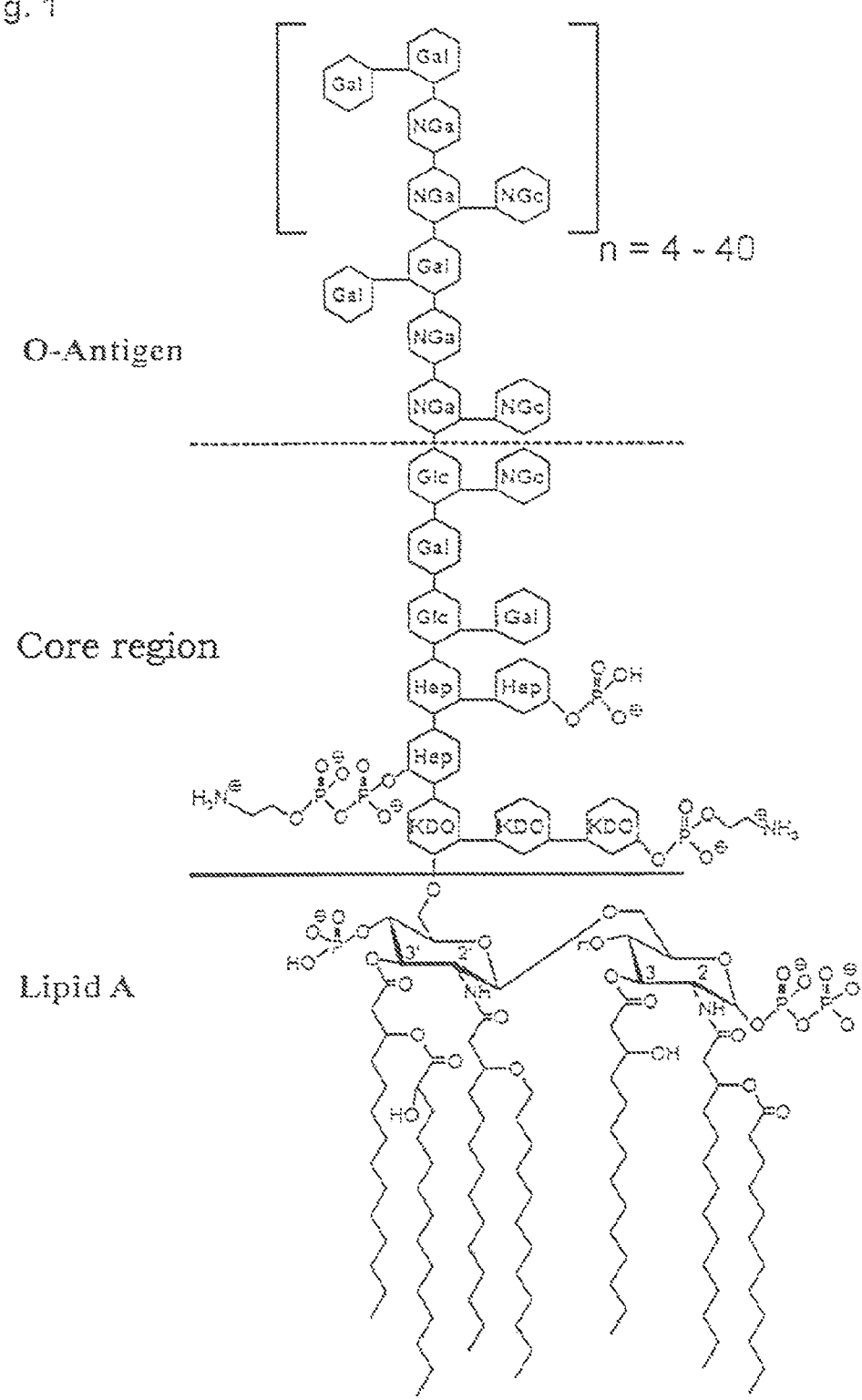
FIG. 1 shows a schematic overview of the chemical structure of endotoxin from E. coli O111:B4. Hep=L-glycero-D-mannoheptose; Gal=galactose; Glc=glucose; KDO=2-keto-3-deoxyoctonate; NGa=N-acetyl-galactosamine; NGc=N-acetylglucosamine.

The term "sample material" or "sample" as used herein comprises any solutions in which endotoxins are to be detected. Examples for solutions are provided in the following list: aqueous solutions and mixtures of water and organic solvents, blood, blood products, plasma, serum, urine, media. Examples for solutions are further those in which solid low molecular and/or high molecular substances to be examined or to be purified are dissolved, such as sugar, salts, antibiotics, proteins, DNA, RNA, food stuff, medicaments, vaccines, or organic and inorganic chemicals like for example NaCl, $MgCl_2$, purine or pyrimidine.

The term "endotoxin" as used here describes bacterial lipopolysaccharide which is a component of the outer membrane of Gram-negative bacteria. "Endotoxin" not only refers to the complete lipopolysaccharide but also to the single components such as lipid A, the inner and the outer heart region.

The term "bacteriophage tail protein" as used here describes those proteins which occur in bacteriophages and can bind endotoxins. Normally, these proteins are localised in the bacteriophage tail but can also be localised on the bacteriophage head or on the normal bacterial shell in the case of bacteriophages without a tail. The term bacteriophage tail protein comprises short as well as long bacteriophage tail proteins. In this respect, bacteriophages with a basal plate (e.g. myoviridae such as T4 like phages) can have different bacteriophage tail proteins, so called long or short bacteriophage tail proteins, which also have different specificities for structures on bacterial membranes.

The term "homology", as used herein, refers to a significant similarity of an amino acid sequence to a reference sequence or parts thereof. The homology of a sequence is determined using the similarity algorithm BLAST (Basic Local Alignment Search Tool, Altschul et al., Journal of Molecular Biology 215, 403-410 (1990). Sequences are regarded as "significant similar", as used herein, which exhibit a homology of at least 60% or which exhibit, for example by using standard parameters in the BLAST-service of NCBI, a significance level (E-value or probability) of $P<10^{-5}$, if they are compared with the reference sequences.

The term "non-specific immobilisation" or "undirected immobilisation" as used here means that coupling of a protein to a matrix is effected via protein radicals (primary amines) which can be distributed over the entire protein surface. The choice of group used for the coupling of the individual protein molecule is random.

The term "surface" or "carrier", as used herein, comprises all materials to which a coupling or adhesion of a protein molecule is possible, such as for example glass surfaces, chromatography materials, such as agarose or sepharose, plastic surfaces, such as polystyrene or polypropylene, filter materials, such as cellulose.

The term "directed immobilisation" as used here means that coupling is effected via amino acid radicals or other radicals (e.g. glycosylations of the protein), the position of which in the protein (e.g. N- or C-terminal) is known. The choice of these groups for the coupling is effected by the choice of suitable reaction partners/linkers which react preferably with these radicals (e.g. coupling of sulfhydryl radicals to iodoacetate radicals; iodoacetate reacts a thousand times more quickly with sulfhydryl radicals than with amino radicals).

One aspect of the present invention relates to a method for detecting endotoxin, comprising the steps:
a) incubation of a sample with bacteriophage tail proteins, and subsequently
b) detection of endotoxin bonded to bacteriophage tail proteins by means of spectroscopic methods, ELISA, chemical and enzymatic detection reaction of endotoxins or cleaved-off Endotoxin components, or by means of capacitance measurement.

If necessary, after step a) and before step b), an additional step a') of separation of bacteriophage tail protein-endotoxin complex from the sample, is introduced.

The detection by means of spectroscopic methods can be implemented by, for example, fluorescence emission, fluorescence polarisation, absorption or circular dichroism, the detection by means of capacitance measurement can be implemented for example by electrical signals. The listed detection methods can further be combined with a competition detection.

The present invention relates preferably to a method, in which after separation of the in step a) formed bacteriophage tail protein endotoxin complex from the sample, the detection of the endotoxins occurs by immunological, chemical or enzymatic reactions. For that purpose the bacteriophage tail proteins can be bound to the respective carrier such as sepharoses or magnetic beads, which are coated with streptavidin or streptactin, by using special ligands such as biotin, strep tag or his tag. Afterwards, if desired, a separation of the coarse-grained carriers from the sample can occur by filtration, centrifugation or magnetic separation. The separation is preferably desired, if the bacteriophage tail protein endotoxin complex is fixed to a surface, which can not be used in the applied detection methods.

The immunological detection is effected for example by binding of endotoxin specific antibodies to the endotoxins, binding of a secondary antibody to the primary antibody and subsequent detection via an enzymatic reaction, which is catalysed by an enzyme fused to the secondary antibody (ELISA).

The endotoxin detection can also occur after chemical cleavage of the endotoxin by acid or base and subsequent detection of single endotoxin components such as 2-ketodesoxyocton acid, the heptoses (Lee C.-H., Tsai C.-M., Analytical Biochemistry, 1999; 267:161-168) or the hydroxyl fatty acids (Lyngby J., Olsen L. H., Eidem T., Lundanes E., Jantzen E., Biologics, 2002; 30:7-13).

In a further aspect the present invention relates to a method for detection of endotoxin, the method comprising the steps of:
a) Contacting a sample containing endotoxins with a carrier, subsequently
b) incubating of bacteriophage tail proteins with the endotoxin immobilised on the carrier, and
c) detection of bacteriophage tail proteins by means of spectroscopic methods, ELISA, chemical or enzymatic detection reaction for endotoxins or cleaved off endotoxin components, or by means of capacitance measurement.

If necessary, after step b) an additional step b') of separation of bound bacteriophage tail proteins from endotoxin, is performed.

Particularly preferred are the p12 proteins of the phages K3, T2, T4, Ox2, RB32-33, AR1, PP01 or RB69.

A method is preferred, in which after the binding of endotoxin to a surface, which carries endotoxin binding ligands such as polymyxin B, poly L lysin, chitosan or the like, bacteriophage tail proteins bind to the immobilised endotoxins and these bacteriophage tail proteins are detected by means of a subsequent enzymatical reaction. The bacteriophage tail proteins can be detected by an ELISA, which is specific for the bacteriophage tail protein, or by enzymes, which are fused via genetical engineering or bound via chemical reactions to the bacteriophage tail protein. The enzymes can be, for example, alkaline phosphatase, peroxidase or others.

Preferably, the ion composition of the bivalent ions, e.g. $Ca^{2+}$, $Mg^{2+}$ and/or the pH value is adjusted prior to the incubation step of the methods according to the invention in order to obtain an optimal endotoxin-bacteriophage tail protein binding. Furthermore, during or after incubation, "demasking" of the bonded endotoxin by addition of detergents and/or salts, e.g. Tween, triton NaCl or ammonium sulphate or other substances, e.g. chitosan, sugar or lipids, which accelerate detachment of the endotoxins from e.g. proteins or nucleic acids, is preferred.

The bacteriophage tail protein used for the detection of endotoxin can be a naturally occurring or be molecular-biologically or biochemically modified one.

Particularly preferred are bacteriophage proteins, which bind to highly conserved regions of endotoxin, more precisely, to the heart region of LPS or to lipid A. Particularly preferred are the short bacteriophage tail proteins preferably of myoviridae phages. However, the endotoxin binding proteins of a bacteriophage head or the normal bacteriophage coat of bacteriophages without tail can be used as well. Exceptionally preferred are bacteriophage tail proteins with a homology of at least 60% on the amino acid level to the p12 protein of T4.

The bacteriophage tail protein can be modified by genetic engineering and/or biochemically for various reasons. For the methods according to the invention, not only the naturally occurring bacteriophage tail proteins can however be used, but also their variants. In the sense of the present invention, variants means that the bacteriophage tail proteins have an altered amino acid sequence. These can be obtained by screening of the naturally occurring variants or by random mutagenesis or targeted mutagenesis, but also by chemical modification. The bacteriophage tail proteins used for the methods according to the invention can be adapted by targeted or random mutagenesis in their specificity or their binding properties to carrier structures. This binding to the carriers can be effected permanently, e.g. covalently or via a specific or non-specific biotinylation, but also can be effected reversibly, e.g. via a reducible disulfide bridge. Furthermore, the stability can be increased by a modification. By means of the molecular-biological or chemical mutagenesis, mutations are introduced which can be amino acid additions, -deletions, -substitutions or chemical modifications. These mutations can effect a change in the amino acid sequence in the binding region of the bacteriophage tail proteins, with the aim of adapting specificity and binding affinity to test requirements, e.g. increasing the binding of the endotoxins to the bacteriophage tail proteins or making them irreversible in order to improve detection. Furthermore, a genetically engineered or biochemical modification of the phage proteins can be implemented with the aim of switching off the possibly present enzymatic activity in order consequently to improve the binding or to make it irreversible. Furthermore, a genetically engineered or chemical modification of the phage proteins can be implemented in order to adapt the present physical properties of the protein, such as solubility, thermal stability etc., in the sense of the method according to the invention.

Furthermore, coupling of the bacteriophage tail proteins with enzymatically active proteins can be performed in order to be able to detect the bacteriophage proteins more sensitively. Enzymatically active proteins like alkaline phosphatase or horseradish peroxidase, for which commercial substrates are available, can be coupled to the bacteriophage tail proteins by means of chemical coupling methods or by means of genetical fusion. The enzymatic reaction introduced via these proteins increases the sensitivity of the detection significantly.

Work to explain the three-dimensional structure of T4 p12 had shown that, at increased temperature, proteolytic fragments of 33 kDa and 45 kDa can be produced, the N- and C-terminal (33 kDa) or only N-terminal (45 kDa) are shortened. In contrast to the 33 kDa fragment, the 45 kDa fragment is still able to bind to bacteria (Thomassen, E., et al., Mol. Biol.; 331: 361-373, 2003). Consequently, the C-terminus is involved in the cell binding. Thus, by a N terminal modification a directed binding to the surfaces can be performed and thus ultimately the binding of endotoxin can be optimised indirectly. Furthermore, a direct optimisation of the endotoxin binding is possible.

The modification can furthermore have the purpose in particular of enabling direct detection, e.g. by means of measurement of the tryptophan fluorescence. For example T4p12 has five tryptophan radicals. The fluorescence spectrum of the native protein indicates that these radicals are extensively solvent-inaccessible. It is known from a multiplicity of scientific works that aromatic amino acids are almost always involved in the binding of sugar radicals, as occur also in endotoxin. The binding of the sugar radicals to proteins can be followed by a quench of the tryptophan fluorescence or if necessary also in addition by changing the fluorescence maximum. It can be supposed from some works that the unfavourable distribution of the fluorophores of natural p12 prevents exploitation of the fluorescent properties of p12 for binding measurement. The fluorescence properties of p12 are dominated by the five tryptophan radicals, the fluorescence of which is altered by the addition of endotoxin in a non-measurable manner. It is expected from these data that rather tyrosine radicals are involved as tryptophan radicals in the binding, the signal alteration of which cannot be made visible in front of the high tryptophan background. On the basis of the proteolysis results, six tyrosines on the C-terminus of p12 are possible for the endotoxin detection kit which can be made correspondingly "visible". By means of a selective molecular-biological exchange of the five tryptophan radicals for tyrosines, the spectroscopic properties are specifically altered in a first step such that the endotoxin binding by fluorescence signal alteration of a single tryptophan radical is measurable. Subsequently, by means of a specific exchange of respectively one of the six tyrosines in the C-terminal region for a tryptophan radical, the intensity of the measurable signal is significantly increased in order to obtain attractive signal differences for the development of an endotoxin-detection kit. As shown for the p12 protein of T4, other short bacteriophage tail proteins such as for example those from myoviridae phages such as T4, T2, K3, Ox2, RB32-33 or RB69 can also be modified accordingly. However, also in this case the endotoxin binding proteins of a bacteriophage head or the normal bacteriophage coat of bacteriophages without tail can be used as well, in particular of PhiX 174.

The bacteriophage tail proteins which are used depends upon which endotoxins are intended to be detected or drawn off. Even now, a large number of known bacteriophages is available for a large part of the previously described bacteria and can be used for the methods according to the invention. The phages and the corresponding host bacteria are inter alia obtainable in the case of the following strain collections: ATCC (USA), DSMZ (Germany), UKNCC (Great Britain), NCCB (Netherlands) and MAFF (Japan); or can be isolated from environmental samples by means of microbiological standard methods. Bacteriophage proteins can be derived from the family of myoviridae, thus can be the tail proteins, in particular from the group of pseudo T even, schizo T even or the T even phages. Preferably the short bacteriophage tail proteins of the phages K3, T2, T4 Ox2, RB32-33, AR1, PP01 and RB69 or the endotoxin binding proteins of the bacteriophages without tail such as PhiX 174 are used for the detection methods according to the invention.

Preferably, the bacteriophage tail proteins for the methods according to the invention stem from bacteriophages, the host bacteria of which have relevant significance with respect to medicine or biotechnology, such as e.g. *E. coli* which is used in the production of recombinant proteins or of nucleic acids for gene therapy. The bacteriophage tail proteins which bind highly conserved regions of endotoxin, such as e.g. the core region or lipid A, are particularly preferred. In particular, T4p12 and T4p12-similar bacteriophage tail proteins are preferred such as T2-p12, K3-p12 (Burda-MR, Hindennach-I, Miller-S, Biol. Chem. 2000; 381: 255-258). In a combination of endotoxin impurities from various host bacteria, a combination of the corresponding endotoxin-detecting bacteriophage tail proteins can be used for the detections or depletions according to the invention.

The detection of endotoxin in or from a sample is effected via the binding of endotoxin to the bacteriophage tail proteins. This binding can be detected for example by direct measurement by means of spectroscopic methods, e.g via fluorescence emission, fluorescence polarisation, absorption or circular dichroism. Furthermore, the binding can be made visible by electrical signals, e.g. a capacitance measurement. Furthermore, the binding of endotoxin to the bacteriophage tail proteins can also be detected indirectly via displacement experiments.

In addition, the binding of bacteriophage tail proteins to endotoxin can be detected by means of first mobilising the endotoxins via other endotoxin binding substances or also via a second bacteriophage tail protein on a surface, followed by the binding of another bacteriophage tail protein to endotoxin. After washing away excess bacteriophage tail protein the amount of the bound other bacteriophage tail protein is subsequently quantified. This is achieved either by means of antibodies directed against the other bacteriophage tail protein (a so called ELISA), or by means of an enzymatic reaction catalysed by a protein, which is fused to the other bacteriophage tail protein. For this purpose the surface can be coated with endotoxin binding substances in advance, such as polymyxin B, histidine, histamine, poly L lysine, DEAE, polyethyleneimine, deoxycholic acid, poly γ-aminomethyl L glutamine, polyvinyl alcohol, poly N,N dimethylaminopropylacrylamide, dextran, chitosan, and the like. Furthermore, a bacteriophage tail protein can be used for the immobilisation of endotoxin. The detection of endotoxin is achieved then with a second bacteriophage tail protein, having other endotoxin binding properties than the bacteriophage tail protein used for the immobilisation. The immobilisation of endotoxin binding substances is achieved either by adhesion, covalent coupling, or by binding via particular immobilisation groups, such as biotin, streptavidin, strep tag, his tag and comparable groups. The detection of the bacteriophage tail protein can also occur after displacement of the protein from the surface.

For the detection methods according to the invention, the bacteriophage tail proteins, if separation of the bacteriophage tail protein-endotoxin complexes from the sample is required, can be coupled to suitable surfaces, e.g. magnetic particles, sepharose particles, agarose particles, microtitre plates, filter materials or throughflow cell chambers (indirect detection). The carrier structures can comprise for example polystyrene, polypropylene, polycarbonate, PMMA, cellulose acetate, nitrocellulose, glass, silicon or agarose. The coupling can be achieved for example by adsorption or covalent binding.

Functional coupling is hereby important, i.e. bacteriophage tail proteins, despite binding to the carrier material, have structures or binding sites, respectively, which are accessible for endotoxin. The coupling of the bacteriophage tail proteins can be effected non-specifically or else preferably directed, via for example a selective biotinylation or coupled or via a spacer or linker.

For this purpose, the bacteriophage tail proteins can be cross-linked with low-molecular substances, e.g. biotin, in order to bind via these low-molecular substances to polypeptides, e.g. streptavidin, which for their part were immobilised on the carrier. Instead of biotin, the so-called Strep-tag (Skerra, A. & Schmidt, T. G. M. Biomolecular Engineering 16 (1999), 79-86) can furthermore be used, which is a short amino acid sequence and binds to streptavidin. Furthermore, the His-tag can be used which, via bivalent ions (zinc or nickel) or an antibody specific for it (Qiagen GmbH, Hilden), can bind to a carrier material. The Strep-tag and the His-tag are bonded preferably via DNA recombination technology to the recombinantly produced bacteriophage proteins. This coupling can be effected directed, e.g. on the N- or C-terminus or at other positions in the bacteriophage tail protein. The directed coupling is effected via a suitable, reactive amino acid, such as cysteine, which is of course not frequently surface-exposed in phage proteins and has been introduced specifically at a suitable position. Since phage tail proteins are synthesised in the cytoplasma, disulfide bridges do not need to be taken into account. Preferably, coupling can take place also via other amino acids, directly or as also with cysteine indirectly via a "spacer" or "cross linker" (monofunctional or bifunctional).

In the case of cysteine coupling, all bifunctional crosslinkers with NH— and SH-reactive groups are possible, with and without intermediate spacers, e.g. 1'-maleimidoundecanoic acid sulfo-NHS or succinimidyl-4-[N-maleimidomethyl]-cyclohexane-1-carboxy-[6-amido]caproate. If no spacers are present, 8-12 C-atom-spacers with a terminal NH group can be inserted. Preferably the cysteine coupling is effected via a specific biotinylation of cysteine by for example EZ-link-PEO-maleimide activated biotin (Pierce).

Bivalent ions, such as e.g. $Ca^{2+}$ or $Mg^{2+}$ are important for binding endotoxins to bacteriophage tail proteins, such as p12 of T4 or the short tail fiber proteins of the phages K3, T2, Ox2, RB32-33, AR1, PP01 or RB69. By adding suitable chelating agents, such as e.g. EDTA or EGTA, this binding can however be broken. For the binding, $Ca^{2+}$ concentrations are preferred in the range of approximately 0.1 µM to approximately 100 mM, particularly preferred in the range of approximately 0.1 µM to approximately 10 mM, and especially preferred in the range of approximately 0.1 µM to approximately 1 mM and furthermore particularly preferred in the range of approximately 10 µM to 1 mM. Furthermore, for the binding, $Mg^{2+}$ concentrations are preferred in the range of approximately 0.1 µM to approximately 10 mM, particularly preferred in the range of approximately 0.1 µM to approximately 1 mM, especially preferred in the range of approximately 10 µM to approximately 1 mM. If the concentration of bivalent ions is lowered by adding 1 mM EDTA under 100 nM, then the binding of endotoxin to p12 is broken. $Mg^{2+}$ concentrations above 10 mM make the binding of endotoxin to p12 worse, which becomes noticeable in an increase in the dissociation constant. Without addition of $Mg^{2+}$, a $K_d$ value of 50 nM is produced and, in a buffer with 10 mM $Mg^{2+}$, a $K_d$ value of 1 µM was measured. Zinc revealed an even higher inhibiting effect. 1 mM Zn increases the $K_d$ value to 10 µM. An adjustment of the concentration of bivalent or other ions (e.g.: $Cu^{2+}$, $Al^{3+}$, $Zn^{2+}$, $Fe^{2+}$, $Ca^{2+}$, $Ba^{2+}$, $Mg^{2+}$, $Cd^{2+}$) to a range which is optimal for the binding, can be effected by substances such as HEDTA, NTA or general chelating agents/buffers (ADA: N-[2-acetamido]-2-iminodiacetic acid; 5-AMP: adenosine-5'-monophosphate; ADP: adenosine-5'-diphosphate; ATP: adenosine-5'-triphosphate; Bapta: 1,2-bis(2-aminophenoxy) ethane-N,N,N',N',-tetraacetic acid; citrate: citric acid; EDTA: ethylene diamine tetraacetic acid; EGTA: ethyleneglycol-bis (β-aminoethyl ether) N,N,N',N'-tetraacetic acid; HEDTA: N-hydroxyethylethylenediaminetriacetic acid; NTA: nitrilotriacetic acid; $SO_4$ sulfate), which can be used as buffers for bivalent ions.

The methods according to the invention can therefore comprise further washing steps. According to whether a direct or indirect detection requires separation of sample and bacteriophage tail protein, washing steps can be incorporated. Since $Ca^{2+}$ or other metal ions (e.g. $Mg^2$) are essential for the binding, the binding of endotoxin to e.g. p12 (e.g. the short tail fiber proteins of phages K3, T2, T4, Ox2, RB32-33, AR1, PP01 and RB69) can be broken by suitable washing steps. According to the aim of whether endotoxin is intended to remain bonded on the bacteriophage tail protein, e.g. p12 (e.g. the short tail fiber proteins of phages K3, T2, T4, Ox2, RB32-33, AR1, PP01 and RB69), washing takes place with EDTA-free buffer, if the binding is intended to be broken, with EDTA-containing buffer, the EDTA concentrations being in the range of at least 0.05 mM to more than 10 mM, preferably in the range of 2 mM to 5 mM.

Since ionic interactions can fundamentally always be affected by changes in the ion strength, increases or reductions of other salts in the solution, such as e.g. NaCl or KCl, can also affect the binding of endotoxin to the bacteriophage tail proteins.

In order to make the binding visible directly or indirectly in the detection method, the protein can also be altered molecular-biologically or biochemically in order to enable measurement or to improve it. In order to make binding of endotoxin e.g. to p12 of T4 or to the short tail fiber proteins of phages K3, T2, T4, Ox2, RB32-33, AR1, PP01 or RB69, or to endotoxin binding proteins of bacteriophages without tail, directly visible, a molecular-biological exchange of tyrosine radicals for tryptophan can be implemented. It can thereby be necessary for a reduction in the signal background to exchange the originally contained tryptophans for tyrosines. In order to be able to make measurements also in protein-containing solutions, p12 of T4 or the short tail fiber proteins of phages K3, T2, T4, Ox2, RB32-33, AR1, PP01 or RB69 can be modified chemically in addition after tryptophan introduction. Tryptophan radicals are thereby altered by Koshland reagent (2-hydroxy-5-nitrobenzylbromide) with respect to their spectroscopic properties. In the case of displacement experiments, marked, e.g. fluorescence-marked endotoxin (e.g. Sigma) can be displaced by endotoxin, e.g. by p12 of T4 or by the short tail fiber proteins of phages K3, T2, T4, Ox2, RB32-33, AR1, PP01 or RB69 or by e.g. PhiX 174, which is located in the sample and the concentration of free fluorescent endotoxin can be determined.

With the methods according to the invention, endotoxin can be detected in all aqueous solutions. These solutions can contain: proteins, plasmid-DNA, genomic DNA, RNA, peptidoglycans, polysaccharides, protein-nucleic acid complexes, such as e.g. phages or viruses, saccharides, vaccines, drugs, reaction buffers, buffer solutions in general, media, dialysis buffers (medicine), salts, blood, blood constituents, or other substances contaminated by endotoxin binding.

A further aspect of the invention is bacteriophage proteins, to which the so-called tags, e.g. the Strep- or His-tag, are coupled preferably to the N- or C-terminus of the protein, particularly preferred to the C-terminus. The coupling or cross-linking of the tags with the bacteriophage proteins via DNA recombination technology is preferred. Production of the nucleic acid, comprising the sequence of the bacteriophage protein and of the tag and the production of the expression product are the state of the art and do not require to be explained here separately. A further aspect of the invention is the nucleic acid sequence which encodes a bacteriophage protein together with the Strep- or His-tag. The p12 protein of the phage T4 is a particularly preferred bacteriophage protein which is modified with the Strep- or His-tag but all other bacteriophage proteins, which are involved in detection and binding of bacteria or are responsible for this, are likewise preferred.

For the methods according to the invention preferably bacteriophage proteins with a tag are used, which has a surface-exposed cysteine for specific directed biotinylation, e.g. the tags according to SEQ ID NO: 5, 6 and 7. An example of a p12 with a tag is the amino acid sequence cited in SEQ ID NO: 8. A p12 with a tag is preferred, in particular with a tag with a surface-exposed cysteine, in particular a p12 with the tag according to SEQ ID NO: 6 and 7. This directed biotinylation can be imparted in addition by a suitable spacer or linker.

The methods according to the invention, relative to the prior detection methods for endotoxin, offer advantages in the performance of corresponding applications. Furthermore, the production of antibodies against LPS core oligosaccharides is very difficult, which renders corresponding methods based on antibodies very expensive.

The present invention further relates to a endotoxin detection kit comprising the components required for the method according to the invention. The kit comprises in particular a carrier coated with the bacteriophage tail proteins as mentioned herein, a container containing a reference endotoxin for the preparation and measurement of a standard curve, a further container with at least one further bacteriophage tail protein described herein, which is if necessary, modified for the detection as mentioned herein or which can be coupled to an active protein, or a container with anti lipid A antibody for the detection of endotoxin.

The following examples explain the invention and should not be understood as restrictive. If not otherwise indicated, molecular-biological standard methods were used, such as e.g. described by Sambrook et al., 1989, Molecular cloning: A Laboratory Manual $2^{nd}$ edition, Cold Spring Harbor Laboratory Press, Cold Spring Harbor, N.Y.

Hereinafter described experiments were performed with p12 proteins of T4, T2 and K3. If not stated explicitly otherwise, the results were only displayed for p12 of T4, as the results of the three proteins are interchangeable due to the high homology (Burda M. R., Hindenach I., Miller S., Biol. Chem. (2000) 381, 225-258; Riede I., Mol Gen Genet. 1987 January; 206 (1):110-115). This also applies for the other proteins displayed in FIGS. 7A-B.

Example 1

Glass Vessels, Plastic Vessels and Buffers

For the endotoxin removal, all the glass vessels were depyrogenated by heating at 200° C. (4 h) and exclusively pyrogene-free plastic materials (e.g. pipette tips, microtitre plates) were used. Other non-heat resistant appliances or vessels were treated either with 3% hydrogen peroxide or washed with 1% sodium deoxycholate. Subsequently, they were rinsed with endotoxin-free water. The buffers were produced from extensively endotoxin-free buffer substances (Sigma) and mixed with endotoxin-free water. Salts, such as e.g. NaCl, which can be heated to 200° C., were heated up (200° C., 4 h). Buffers used for chromatographic purifications were degassed and filtered.

Example 2

Endotoxin Detection by Means of LAL Test

Endotoxin control tests were implemented with a chromogenic LAL test (Limulus-Amoebocyte-Lysate test, Charles-River Endosafe, Charleston, USA) corresponding to the instructions of the producer. In order to determine the concentrations, endotoxin standards (Charles-River Endosafe, Charleston, USA) in the range of 0.005-50 or 0.02-50 EU/ml were used. The absorption measurement at 405 nm took place in a temperature-controlled microtitre plate reader (Genios, Tecan GmbH).

Example 3

Western-Blot for p12 Detection

The detection of p12 in the residue of samples treated with beads or in the fractions of the affinity chromatography was effected by Western Blots. In part, the proteins were concentrated in advance by NaDOC/TCA precipitation (sodium deoxycholate/tetrachloroacetate). The samples were electrophoretically separated for this purpose on 12% SDS gels and transferred onto PVDF membranes (Immobilon, Millipore). The membranes were washed with PBS for 30 min, blocked with 5% milk powder (1 h) and subsequently incubated with polyclonal anti-p12 antibody (1 h, dilution: 1: 1000). After incubation with a secondary antibody (goat-anti-rabbit IgG), conjugated with alkaline phosphatase, the development of the samples was effected with BCIP/NBT (5-bromo-4-chloroindolylphosphate/nitroblue tetrazolium salt).

Example 4

Endotoxin Purification

The purification of endotoxin was implemented according to the specification of Galanos, C., Lüderitz, O. & Westphal, 0.1969, Europ. J. Biochem. 9, 245-249.

Example 5

Specific Coupling of p12 to Immobilised Iodoacetyl Radicals

In order to achieve a directed binding of p12 to the surface, the amino acid serin at position 3 of the Strep-tag according to SEQ ID NO:5 was replaced by cysteine as in example 12 and the protein was immobilised via iodoacetyl radicals which bind preferably free sulfydryl radicals. The resulting p12 was called p12S3C.

A 1 ml Sulfolink Coupling Gel (Pierce) was poured out, washed with 6 ml 1% sodium deoxycholate and equilibrated with 6 ml coupling buffer (50 mM tris, 150 mM NaCl, 5 mM EDTA, pH 8.5). Subsequently, 1 ml p12S3C (=N-strepS3 Cp12) was injected (1-1.5 mg/ml in coupling buffer), the column was agitated gently for 15 min, incubated for a further 30 min without agitation at room temperature, and 12S3C was injected again and the incubation steps were repeated. This coupling of p12S3C was repeated in total 4 times, and subsequently the column was washed with 6 ml coupling buffer. The throughflows were collected and the respective p12S3C concentration was determined by absorption measurement at 280 nm. 2.2-2.8 mg p12S3C per ml gel were bonded. Subsequently, surplus iodoacetyl radicals were blocked by incubation (45 min) with 1 ml cysteine (50 mM in 50 mM tris, 5 mM EDTA, pH 8.5). After washing the column with 16 ml 1M NaCl and 16 ml 20 mM hepes, 150 mM NaCl pH 7.5, the column was ready for use.

Figure 2:
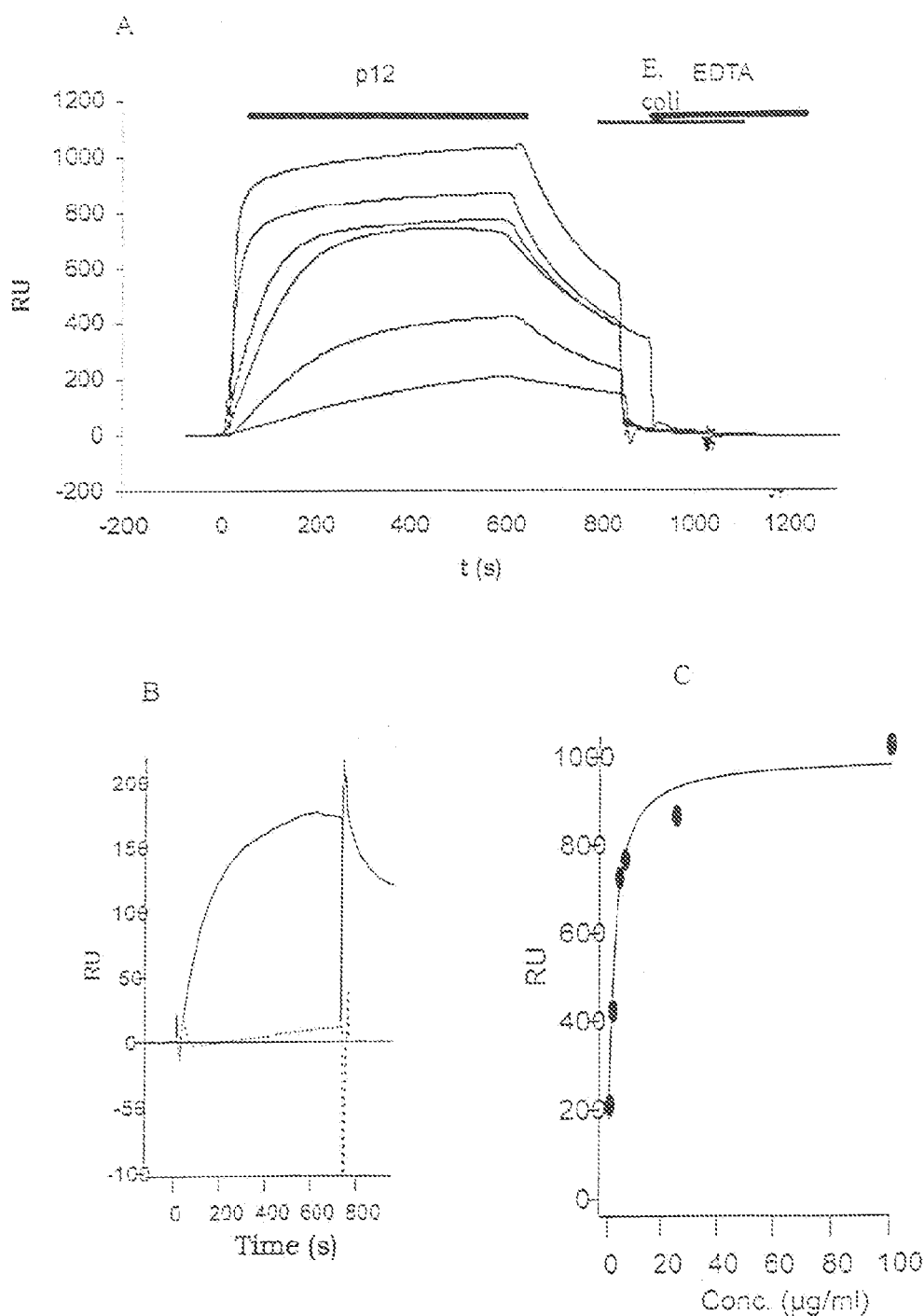
FIG. 2 shows results of surface-plasmon-resonance measurements. (A) Resonance curves which were measured as response to injection of various (respectively in µg/ml: 100; 25; 6.25; 4; 1.56; 0.4) p12 concentrations (_____). Binding is effected on endotoxin from E. coli D21f1 which was immobilised on a hydrophobic HPA chip. The injection of p12 and EDTA (5 mM) is marked via bars over the curves. Buffer: 20 mM tris, 150 mM NaCl, pH 8.0. (B) Equilibrium resonance values for the binding of p12 to immobilised endotoxin were measured approximately 600 s after the beginning of the p12 injection and plotted against the associated p12 concentration. The continuous line shows a fit of the Langmuir adsorption isotherms ($RU=RU_{max}*[p12]/[p12]+K_d)$) to the data. (C) Binding of E. coli to biotinylated p12 which was immobilised on streptavidin chips. E. coli D21e8 (_____) the inner core region of which is complete, to p12. In contrast, E. coli D21f2 ( - - - ), which has a greatly shortened core region, does not bind to p12. The measurements were implemented in PBS.

The capacity of this gel to remove endotoxin from protein solutions was tested with BSA (2-4 mg/ml), carbonic anhydrase (1-2 mg/ml) and lysozyme (3-4 mg/ml). BSA and lysozyme solutions were spiked with endotoxin from *E. coli* O55:B5 (Charles-River Endosafe, Charleston, USA) or *E. coli* HMS 174 (100-1000 EU/ml), whilst the carbonic anhydrase was not mixed with additional endotoxin. Respectively 0.5 ml protein solution was introduced to the column, incubated for 1 hour at room temperature and subsequently the column was washed with buffer. The proteins were collected in fractions and the endotoxin content, prior to and after the column, was determined by means of a chromogenic LAL test (Charles-River Endosafe, Charleston, USA). In addition, the protein retrieval was determined by absorption measurements at 280 nm. The endotoxins were able to be removed almost completely (93-99%) from all 3 protein solutions, as shown in FIG. 2A. In addition, the proteins were able to be eluted extensively from the column (80-99%, FIG. 2B). The column was finally regenerated with 5 mM EDTA, 20 mM hepes, 150 mM NaCl, pH 7.5. In order to exclude impurities of the protein fractions after running over the column due to separating p12, the fractions were tested for p12 by means of the Western Blot technique. No p12 was able to be detected in the fractions.

Example 6

Non-Specific Coupling of p12 to NHS-Activated Carrier Material

N-hydroxysuccinimide (NHS) is displaced from compounds by primary amino radicals and therefore is used to couple proteins to surfaces. NHS-activated sepharose columns (HiTrap NHS-activated HP, 1 ml, Amersham-Pharmacia-Biotech) were washed firstly with 6 ml ice cold 1 mM hydrochloric acid. Subsequently, 10-15 ml p12S3C (1.0-3.5 mg/ml) in 0.2 M $NaHCO_3$, 0.5 M NaCl, pH 8.3 were pumped in a circle over the column at room temperature (flow rate 0.8 ml/min). After 60 min, the throughflow was collected in fractions and the column was washed with 6 ml buffer. From these fractions, the NHS was separated by desalting the solution via HiTrap-desalting column (5 ml, Amersham-Pharmacia-Biotech) and subsequently the p12 quantity was determined by absorption measurement at 280 nm. 20-25 mg p12S3C were bonded to the column. The column was rinsed after the coupling corresponding to the instructions of the producer repeatedly with respectively 6 ml blocking buffer (0.5 M ethanolamine, 0.5 M NaCl, pH 8.3) and washing buffer (0.1 M acetate, 0.5 M NaCl, pH 4.0). Subsequently, the column was equilibrated with 6 ml usable buffer (20 mM hepes, 150 mM NaCl, pH 7.5 or 20 mM tris, 150 mM NaCl, pH 8.5).

The endotoxin removal via this column was tested with lysozyme solutions (3-4 mg/ml in 20 mM hepes, 150 mM NaCl, pH 7.5 or 20 mM tris, 150 mM NaCl, pH 8.5). The lysozyme solutions were spiked with endotoxin from *E. coli* HMS 174 (~500 EU/ml). 0.5 ml protein solution were introduced onto the column, incubated for 1 hour at room temperature and subsequently the column was washed with buffer. The lysozyme was collected in fractions and the endotoxin content was determined prior to and after the column by means of a chromogenic LAL test (Charles-River Endosafe, Charleston, USA). In addition, the protein retrieval was determined by absorption measurements at 280 nm. The endotoxins were removed up to 85-90% from the solution, as shown in FIG. 3A, and 85-90% of the lysozyme were able to be eluted again from the column by means of washing with usable buffer (FIG. 3B). The column was subsequently washed with 6 ml 5 mM EDTA, 20 mM hepes, 150 mM NaCl, pH 7.5 and 6 ml 1 M NaCl. In order to exclude impurities of the protein fractions after running over the column due to separating p12, the fractions were tested by means of the Western Blot technique for p12. No p12 was able be detected in the fractions.

Example 7

Directed Coupling of p12 to NHS-Activated Carrier Material Column Via Diaminoethane and N-Succinimidyl-Iodoacetate (SIA) as Spacer In order to achieve a directed binding to the chromatography carrier material, a bifunctional linker was bonded to NHS-activated surface, which linker made a coupling of p12S3C possible via its free cysteine and iodoacetyl radicals of the bifunctional linker.

NHS-activated sepharose columns (HiTrap NHS-activated HP, 1 ml Amersham-Pharmacia-Biotech) were washed firstly with 6 ml ice cold 1 mM hydrochloric acid, thereafter 1 ml ethylene diamine (10 mg/ml in 0.2 M $NaHCO_3$, 0.5 M NaCl, pH 8.3) was injected and the column was incubated for 30 min at room temperature. After blocking surplus NHS groups with ethanolamine (0.5 M ethanolamine, 0.5 M NaCl, pH 8.3) and washing (0.1 M acetate, 0.5 M NaCl, pH 4.0) of the column, the column was equilibrated with 6 ml borate buffer (50 mM sodium borate, 150 mM NaCl, 5 mM EDTA, pH 8.3). Subsequently, 10 ml N-succinimidyl-iodoacetate (SIA, Pierce, 200 µl SIA parent solution in 10 ml borate buffer; SIA parent solution: 1.4 mg SIA in 1 ml DMSO) was rinsed in a circle over the column for 30 min. The column was thereafter washed with 6 ml borate buffer and p12S3C (1 mg/ml, 50 ml in borate buffer) was rinsed over the column for 1 hour. Excess iodoacetyl radicals were neutralised with 1 ml cysteine solution (5 mM cysteine in borate buffer, incubation at room temperature for 15 min), before the column with the usable buffers (20 mM hepes, 150 mM NaCl, pH 7.5 or 50 mM tris, 150 mM NaCl, ph 8.5) were equilibrated. The coupling reactions with SIA were implemented in the dark.

The endotoxin removal over this column was tested with lysozyme solutions (3-4 mg/ml in 20 mM hepes, 150 mM NaCl, pH 7.5 or 20 mM tris, 150 mM NaCl, ph 8.5). The lysozyme solutions were spiked with endotoxin from *E. coli* HMS174 (~500 EU/ml). 0.5 ml protein solution was introduced onto the column, was incubated for 1 hour at room temperature and subsequently the column was washed with buffer. The lysozyme was collected in fractions and the endotoxin content was determined prior to and after the column by means of a chromogenic LAL test (Charles-River Endosafe, Charleston, USA). In addition, the protein retrieval was determined by absorption measurements at 280 nm. The endotoxins were removed up to 90% from the solution and 75-85% of the lysozyme were able to be eluted again from the column by washing with usable buffer. The column was subsequently washed with 6 ml 5 mM EDTA, 20 mM hepes, 150 mM NaCl, pH 7.5 and 6 ml 1 M NaCl. In order to exclude impurities of the protein fractions after running over the column due to separating p12, the fractions were tested for p12 by means of the Western Blot technique. No p12 was able to be detected in the fractions.

Example 8

Removal of Endotoxin from a BSA Solution in the Throughflow Method

HiTrap-NHS activated sepharose (Amersham Biosciences, Uppsala Sweden) was coupled, according to the specification of the producer, non-specifically via primary amino groups with p12. 8 mg p12 per ml gel material were thereby immobilised covalently. The thus obtained 1 ml chromatography column was equilibrated with a flow rate of 1 ml/min with 10 ml buffer A (20 mM hepes, pH 7.5, 150 mM NaCl, 0.1 mM $CaCl_2$). Next, 4 ml of a BSA solution (11.5 mg BSA (Carl Roth GmbH, Germany)/ml buffer A) were applied (injection: I) and the throughflow (E) was collected in 2.5 ml fractions. The column was washed subsequently with 15 ml buffer A and the endotoxin bonded to the column was eluted with 7 ml buffer B (20 mM hepes, pH 7.5, 150 mM NaCl, 2 mM EDTA). During washing and elution, respectively 2 ml fractions were collected. After each experiment, the column was regenerated with 20 ml buffer C (20 mM hepes, pH 7.5, 150 mM NaCl, 2 mM EDTA, 0.1% sodium deoxycholate). The endotoxin concentration was determined by a chromogenic *Limulus* Amoebocyte Lysate (LAL) (Charles-River Endosafe, Charleston, USA) according to the specification of the producer. Determination of the protein concentration was effected by measurement of the UV absorption. The endotoxin removal efficiency was between 95-99% and the protein loss was approximately 6-10%.

Example 9

Removal of Small Endotoxin Quantities from Buffer by Means of Non-Specifically Coupled p12

20 ml NHS-activated sepharose 4 FastFlow (Amersham Biosciences) were washed firstly with ice cold hydrochloric acid and subsequently incubated with 292 mg p12 (7 mg/ml in 25 mM citrate pH 7.0) for 4 hours at room temperature with agitation. Subsequently, the sepharose was washed with 7×80 ml 5 mM citrate pH 2.0 and respectively 1 ml of the washing fractions was dialysed against 5 mM citrate pH 2.0. These dialysates were used in order to quantify the excess p12 in the washing fractions by means of absorption measurement at 280 nm. A charge density of 8.7 mg p12 per 1 ml sepharose was determined. Non-reacted NHS radicals were neutralised by 12 h incubation of the sepharose with 1M tris pH 8.0. Columns with 2 ml volume were filled with this column material and this was stored until use at 4° C. in 20% ethanol.

In 3 parallel tests, respectively 4 ml endotoxin solution (S) were applied onto a column. The endotoxin solution comprised endotoxin from *E. coli* O55:B5 (Charles-River Endosafe, Charleston, USA) in equilibration buffer (20 mM hepes, 150 mM NaCl, 0.1 mM $CaCl_2$, pH 7.5). The endotoxin concentration of this solution was 4.6 EU/ml.

The column was rinsed firstly with 12 ml regeneration buffer (20 mM hepes, 150 mM NaCl, 2 mM EDTA, pH 7.5) and subsequently with 12 ml equilibration buffer. Subsequently, equilibration buffer was introduced once again to the column and 1 ml was fractionated.

The endotoxin solution was applied onto the columns (I) and fractions of 5 ml and 2 ml were collected. Subsequently, the column was regenerated with 4 ml regeneration buffer (B). In the throughflow fractions, no endotoxin could be detected, i.e. the endotoxin impurities were able to be removed completely in all three experiments. This example illustrates clearly, that binding occurs also at low endotoxin levels, which is equivalent to a detection of low endotoxin.

Example 10

Non-Specific Coupling of Biotinylated p12 to Magnetic Streptavidin Beads p12 (3 mg/ml in PBS, 0.05% Tween20) was incubated with sulfo-NHS-LC-LC-biotin (Pierce), in the ratio 1:10 to 1:20 for 1 hour at RT and subsequently was dialysed against buffer (e.g. PBS or 20 mM hepes, 150 mM NaCl, 5 mM EDTA, pH 7.5). NHS-activated biotin binds thereby to primary amino radicals of p12. Subsequently 50 µl biotinylated p12 (1 mg/ml) were added to 1 ml streptavidin beads (MagPrep streptavidin beads, Merck), were agitated at room temperature for 2 h and subsequently excess p12 was removed by washing four times with 1.5 ml 20 mM tris, 10 mM EDTA, pH 7.5.

The endotoxin removal was tested with buffer (20 mM hepes, 150 mM NaCl, pH 7.5) and protein solutions (0.1 mg/ml BSA, 0.1 mg/ml lysozyme, 0.1 mg/ml carbonic anhydrase in 20 mM hepes, 150 mM NaCl, pH 7.5). The buffer and the BSA and lysozyme solution was spiked with 5 EU/ml (endotoxin from *E. coli* O55:B5, Charles-River Endosafe, Charleston, USA). The carbonic anhydrase solution contained approximately 1 EU/ml. 25 µl magnetic beads with immobilised p12 were added to 200 µl buffer or protein solution, mixed by pipetting up and down and were incubated for 30 min at room temperature. The beads were removed from the solution by means of a magnet, the residue was pipetted off. The endotoxin content of untreated samples and samples incubated with beads was subsequently determined with the LAL test and the protein retrieval was determined by absorption measurement at 280 nm. The endotoxin could be practically completely removed from the buffer (99.9% endotoxin removal) and the endotoxin was depleted also from the protein solution by 70-92%. The protein retrieval was between 57% and 99% (BSA: 87%, carbonic anhydrase: 99%, lysozyme: 57%; FIG. 4B).

Example 11

Non-Specific Coupling of Biotinylated p12 to Immobilised Streptavidin p12 (3 mg/ml in PBS, 0.05% Tween20) was incubated with sulfo-NHS-LC-LC-biotin (Pierce), in the ratio 1:10 to 1:20 for one hour at RT and subsequently dialysed against buffer (e.g. PBS or 20 mM hepes, 150 mM NaCl, 5 mM EDTA, pH 7.5). NHS-activated biotin thereby binds to primary amino radicals of p12. The biotinylated p12 is subsequently incubated for 1 h at room temperature with chromatography material laden with streptavidin (ImmunoPure immobilised streptavidin: 6% cross-linked agarose beads) and excess p12 is removed by washing with PBS.

The endotoxin removal was tested with buffer (20 mM tris, 150 mM NaCl, pH 8.0) and BSA (0.5 mg/ml in 20 mM tris, 150 mM NaCl, pH 8.0). Respectively 1 ml buffer or BSA solution was spiked with 10 EU/ml, 50 µl p12 agarose was added, agitation took place for 1 hour at room temperature. The p12 agarose was centrifuged off subsequently and the endotoxin- and protein concentration in the residue was measured. 99% endotoxin could be removed from the buffer and 86% from the BSA solution. BSA was retrieved up to 90%.

Example 12

Tests Via p12 Endotoxin Binding by Means of Surface Plasmon Resonance Measurements Binding of p12 to endotoxin or to bacteria via the liposaccharides in the outer cell membrane was tested by means of surface plasmon resonance measurements (Biacore J). In order to determine the dissociation constant ($K_d$), endotoxin from *E. coli* O55:B5 (Sigma) was immobilised on a hydrophobic HPA chip corresponding to the instructions of the producer and p12 was injected in various concentrations (FIG. 2A). Binding is measured in relative "response units" (RU), the equilibrium values are plotted against the associated p12 concentrations (FIG. 2B). By adapting the Langmuir adsorption isotherms ($RU=(RU_{max}*[p12])/([p12]+K_d)$) to these data, the $K_d$ value was determined (Table 1). Endotoxin-free buffers were used for the measurements. $K_d$ values in the range of $10^{-7}$ to $10^{-9}$ M were determined for pH values between 6 and 10 (Table 1). The binding was broken again by injection of 1 mM or 5 mM EDTA and the chip was regenerated.

TABLE 1

Dissociation constants of endotoxin on p12 dependent upon the pH value of the solution

| pH | Kd |
|---|---|
| 6.00 | 3.09E−07 |
| 7.50 | 6.85E−08 |
| 8.00 | 5.86E−08 |
| 8.50 | 7.86E−08 |
| 9.00 | 3.29E−08 |
| 10.00 | 1.55E−07 |

In order to test the binding of bacteria to p12, biotinylated p12 was immobilised on streptavidin chips and various *E. coli* strains were injected. The bacteria were absorbed in PBS for the measurements. *E. coli* strains were used which have lipopolysaccharides with different polysaccharide components. The polysaccharide part comprises a "core" region which is cross-linked to the lipid A and to the so-called O antigen. The O antigen varies very greatly between different types of bacteria and also strains of bacteria, whilst the "core" region is highly preserved. Strains, which have the "core" region and O antigen (e.g. *E. coli*), and strains which have a complete "core" region (*E. coli* D21), were bonded by p12, whilst strains with a greatly shortened "core" region (e.g. *E. coli* D21f2) were no longer detected by p12 (FIG. 2C). The binding was able to be broken again by EDTA (5 mM) and the chip was able to be regenerated.

Example 13

Recombinant p12 Constructs

Construction of p12 with N-terminal Strep-tag (N-strep-p12): by means of PCR, the nucleotide sequence for the Strep-tag (U.S. Pat. No. 5,506,121) was introduced to the 5' end of the T4p12 gene. A primer was constructed for this purpose for the 5' end of the p12 gene (5'-GAA GGA ACT AGT CAT ATG GCT AGC TGG AGC CAC CCG CAG TTC GAA AAA GGC GCC AGT AAT AAT ACA TAT CAA CAC GTT-3' (SEQ ID NO:1), which comprises the nucleotide sequence of the Strep-tag at its 5' end (italicised in the sequence) and has a restriction interface (NdeI, underlined in the sequence) such that the gene in the right-hand reading grid can be inserted into the expression plasmid. For the 3' end of the p12 gene, a primer was constructed which introduces, behind the p12 gene, a BamH I restriction interface (italicised in the sequence) (5'-ACG CGC AAA GCT TGT CGA CGG ATC CTA TCA TTC TTT TAC CTT AAT TAT GTA GTT-3'), (SEQ ID NO:2). The PCR was implemented with 40 cycles (1 min 95° C., 1 min 45° C. and 1 min 72° C.). The PCR batch was cut with the restriction endonucleases NdeI and BamHI and the desired fragment was inserted after size fractionation via an agarose gel and elution from the gel into the NdeI and BamHI site of the expression plasmid pET21a. The sequence of the N-strep-p12 gene was checked for its correctness via DNA sequencing. The further steps for the plasmid pNS-T4p12p57 were implemented as described by Burda, M. R. & Miller, S. (Eur J. Biochem. 1999 265 (2), 771-778) for T4p12p57. The plasmid pNS-T4p12p57 was then transformed into the expression strain BL21(DE3).

2. Insertion of an N-terminal cysteine radical in N-strep-p12 (N-strep-S3C-p12 and N-strep-S14C-p12): the insertion of an N-terminal cysteine radical was implemented as described under 1, two new primers for the 5' end being constructed for this purpose. There was used for the N-strep-S3C-p12, the primer 5'-GAA GGA ACT AGT CAT ATG GCT TGT TGG AGC CAC CCG CAG TTC GAA AAA GGC GCC AGT AAT AAT ACA TAT CAA CAC GTT-3' (SEQ ID NO:3), there was used for the N-strep-S14C-p12, the primer 5'-GAA GGA ACT AGT CAT ATG GCT AGC TGG AGC CAC CCG CAG TTC GAA AAA GGC GCC TGT AAT AAT ACA TAT CAA CAC GTT-3' (SEQ ID NO:4).

3. Purification of N-strep-p12 protein: the *E. coli* strain BL21 (DE3) with the plasmid pNS-T4p12p57 was drawn in 2 l shaker cultures (LB medium with ampicillin 100 µg/ml) up to a OD600 of 0.5-0.7 at 37° C. and the expression of the N-strep-p12-protein was induced by addition of 1 mM IPTG (isopropyl-(3-thio-galactopyranoside). After incubation at 37° C. for 4 h, the cells were collected. Collected cells from 10 l culture were taken up in 50 ml sodium phosphate, 20 mM pH 7.2, 2 mM MgSO4, 0.1 M NaCl, broken up by French press treatment (20,000 psi) three times and subsequently centrifuged off for 30 min at 15,000 rpm (SS34). After washing twice in the same buffer, the N-strep-p12 protein was extracted from the pellet, the pellet was extracted three times by agitation for 30 min in 40 mM trisHCl pH 8.0, 10 mM EDTA, the batch was centrifuged for 30 min at 15,000 rpm (SS34) and the dissolved NS-p12 was stored in the residue at 4° C. The extraction was repeated twice and the combined residues were applied (IBA GmbH Göttingen) onto a StrepTactin affinity column (15 ml), equilibrated with buffer "W" (100 mM trisHCl pH 8, 1 mM EDTA, 150 mM NaCl). After washing with 5 column volumes of buffer "W", elution took place with three volumes of buffer "W" with 2.5 mM dethiobiotin in buffer "W". After multiple dialysis against buffer "W" and concentration, the concentration and purity of N-strep-T4p12 was determined via SDS-PAGE and UV spectroscopy (Burda et al. 1999). From 10 liters culture, approximately 100 mg N-strep-T4p12 were thus purified.

| Name | Sequence of the tag | |
|---|---|---|
| Nstrep-p12 | MASWSHPQFEKGAS | SEQ ID NO: 5 |
| Nstrep-p12-S3C | MACWSHPQFEKGAS | SEQ ID NO: 6 |
| Nstrep-p12-S14C | MASWSHPQFEKGAC | SEQ ID NO: 7 |

Example 14

Detection of LPS by Means of Binding of p12 to Immobilised LPS

Figure 4:
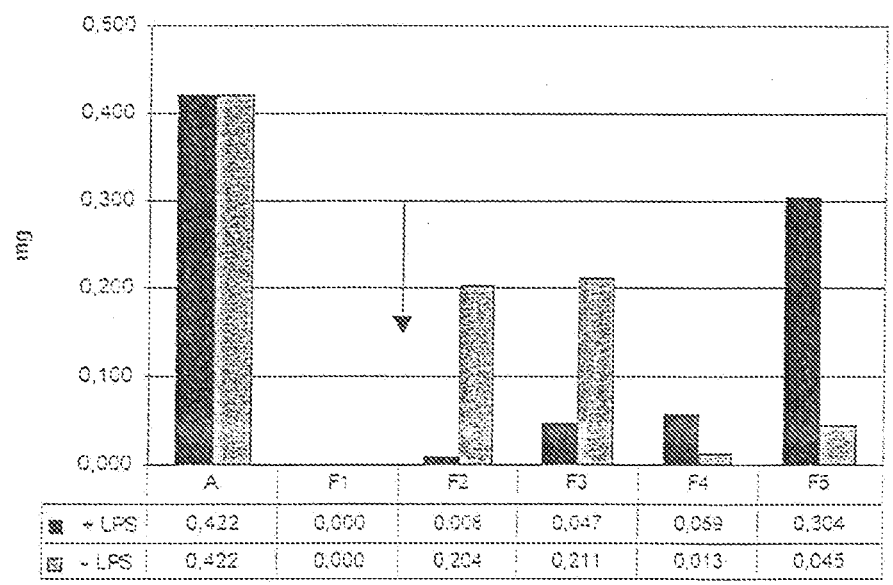
FIG. 4 shows in a bar chart the binding behaviour of the bacteriophage tail protein p12 to endotoxin which is immobilised by polymyxin B on chromatography columns (0.5 ml). Two polymyxin B columns were rinsed with endotoxin of E. coli O55:B5 ($10^6$ EU/ml) (+LPS, black bars), and two columns were washed with water (-LPS, striped bars). The amount of bacteriophage tail protein p12 was plotted against the fractions of the chromatography run. Each bar indicates the mean values determined in two parallel chromatography runs. The first pair of bars (A) display the loaded amount of p12 and the second fraction 1 (F1), a control fraction prior to the loading of p12 onto the column. The arrow indicates the loading of p12 onto the column. Fractions 2-5 were collected after the application. The concentration of p12 was determined after measuring the absorption at 280 nm. The fraction volume for fractions 1-4 was 1 ml and 2 ml for fraction 5. The regeneration of the column in fraction 5 was carried out by addition of 2 mM EDTA to running buffer (20 mM Hepes, 150 mM NaCl, 0.1 mM $CaCl_2$, pH 7.5). The bacteriophage tail protein p12 was retained on the columns previously loaded with endotoxin, whereas it passed without delay through the columns, which did not contain endotoxin.

Four columns with 0.5 ml volume each were cast with polymyxin B sepharose (detoxi gel, Pierce). Each column was washed with 3 ml sodium phosphate buffer (20 mM sodium phosphate, pH 12.0) and 3 ml regeneration buffer (20 mM Hepes, 150 mM NaCl, 2 mM EDTA, pH 7.5). Subsequently, on two of these columns 1 ml LPS per column of *E. coli* O55:B5 was loaded (0.1 mg/ml in Hepes buffer, $10^6$ EU/ml). The two other columns were each rinsed with 1 ml regeneration buffer. After that all columns were each washed with 3 ml equilibration buffer (20 mM Hepes, 150 mM NaCl, 0.1 mM $CaCl_2$, pH 7.5) and subsequently 1 ml of this buffer was loaded once more and eluted as fraction 1. Afterwards 0.5 ml of a solution with the bacteriophage tail protein p12 (0.844 mg/ml in 20 mM Hepes, 150 mM NaCl, 0.1 mM $CaCl_2$) was loaded onto the columns and washed with 2.5 ml equilibration buffer and 2 ml regeneration buffer. The flow through was collected in fractions of three times 1 ml and once 2 ml, and the concentration of the bacteriophage tail protein p12 in these fractions was determined by means of absorption measurement at 280 nm (FIG. 4). The vast majority of the bacteriophage tail protein p12 was bound to the columns, which had been pre-treated with LPS, and was elutable from these columns by addition of regeneration buffer. In contrast, it passed through the columns not pre-treated with LPS without delay.

Example 15

Detection of the Binding of Endotoxin Polysaccharide to the T4p12 Mutant W359Y W283Y In the used T4p12 mutant the amino acid tryptophan at positions 359 and 283 is substituted by tyrosine For the fluorescence analysis a polysaccharide (MW=2 kDa) derived from the endotoxin of *Salmonella typhimurium*, was used. The p12 mutant (40 or 200 µg/ml) as well as the endotoxin polysaccharide were dissolved in 5 mM citrate pH 2. The fluorescence in the range of 305-450 nm was measured at an excitation of 295 nm. Of 120 µl of a solution with the p12 mutant W359Y W283Y provided in a fluorescence cuvette, the fluorescence was measured and subsequently polysaccharide was added stepwise (final concentration: 0.5-120 000 nM) and after mixing the sample the fluorescence was measured anew. In control experiments the same experiment was carried out without the p12 mutant and the measured curves were corrected with this data.

Figure 5:
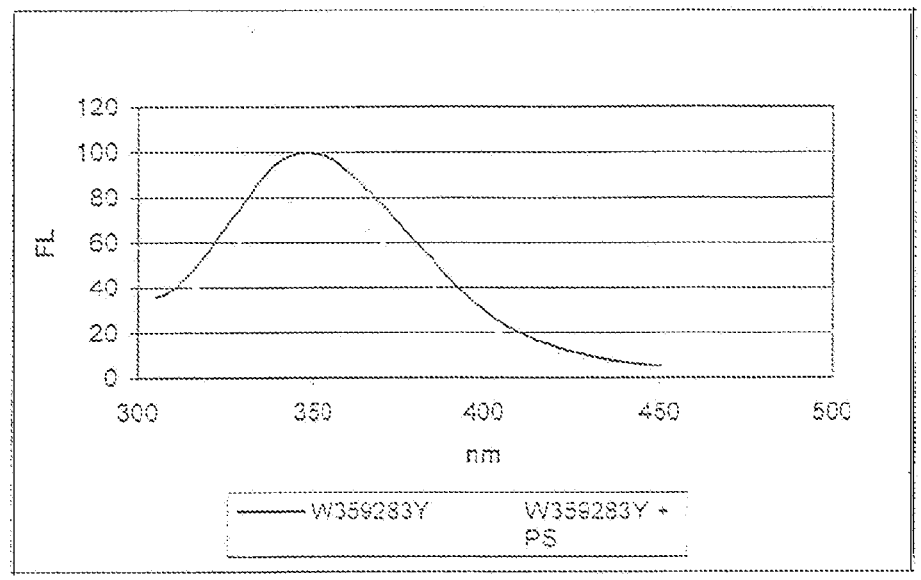
FIGS. 5 A and B display in a chart the decrease of fluorescence of T4p12-mutante W359_283Y after addition of endotoxin polysaccharide (from salmonella thyphimurium). A) the fluorescence of the p12 mutant W359_283Y (40 µg/ml) in the range of 305-450 nm was measured at an excitation of 295 nm. After addition of 3 µl polysaccharide (10 mg/ml) (grey curve) to a 120 µl solution containing p12-mutant W359_283Y, a decrease in fluorescence could be observed in comparison to the untreated sample (black curve). The curves were corrected against control measurements without the p12 mutant. Figure B shows the decrease of fluorescence in percent of the p12 mutant W359_283Y against the concentration of the applied endotoxin polysaccharides. The excitation wave length was 295 nm and the emission wave length 350 nm. The p12 mutant W359_283Y (200 µg/ml or 3.6 µM) was provided first and titrated with endotoxin polysaccharide. On the x axis the final concentrations of the endotoxin polysaccharides are plotted. The measured values were corrected against control measurements without the p12 mutant W359_283Y. Beginning with a polysaccharide concentration of 500 nM a significant reduction of fluorescence could be measured.
Figure 5:
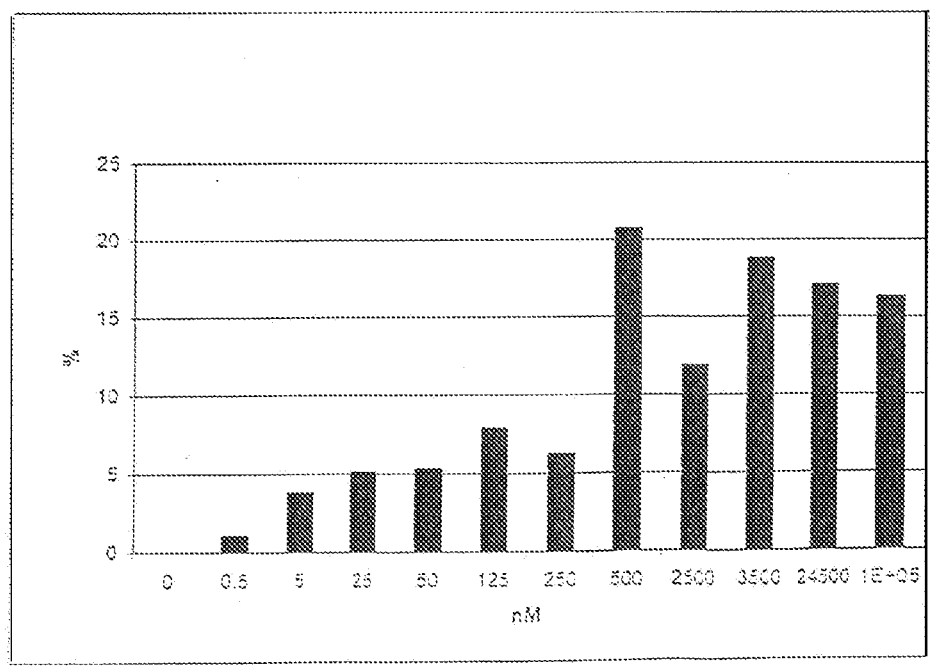

The binding of endotoxin or of an endotoxin polysaccharide reduces the fluorescence of this mutant (FIG. 5). This can be used for the detection of endotoxin.

Example 16

Immobilisation of Lipopolysaccharide Via T4p12 and Detection of the Binding Via an Anti Lipid a Antibody For the detection lipopolysaccharides are bound first from a sample solution to a surface and subsequently these immobilised lipopolysaccharides are detected by means of a second protein binding to the lipopolysaccharides. To illustrate the feasibility of this detection method, such a "sandwich" was constructed on the surface of a Biacore chip and the binding of lipopolysaccharide and a lipid A antibody was monitored by means of surface plasmon resonance measurement.

Figure 6:
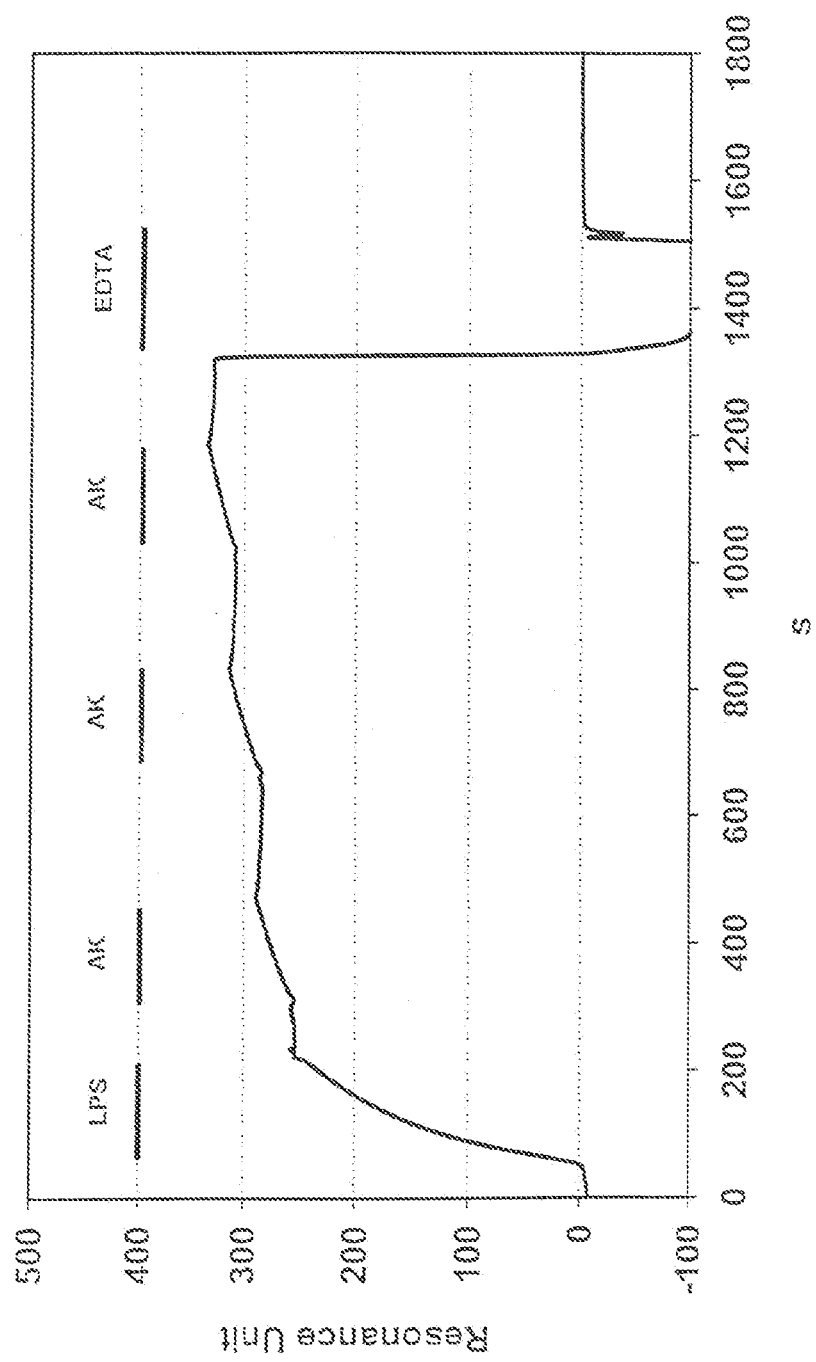
FIG. 6 shows the binding of an anti-lipid A antibody to lipopolysaccharide bound via T4p12 to a surface. The binding was observed by measuring the surface plasmon resonance signals using a Biacore J. According to the instructions of the manufacturer, T4p12 was covalently immobilised in a flow through chamber (CM-5 chip from Biacore) via primary amino groups. Subsequently, lipopolysaccharide of E. coli O55:B5 (LPS, 0.1 mg/ml) was injected. The injection phases are indicated as bars above the measured curve. The increase of resonance signal shows the binding of lipopolysaccharide to T4p12. Even after finishing the injection the resonance signal remains increased and therewith the lipopolysaccharide bound to the surface. Subsequently, an antibody (Ab) directed against lipopolysaccharide was injected three times (2 µg/ml, polyclonal antibody against lipid A from Accurate Chemical & Scientific Corporation). The increase of the resonance signal with each injection indicated the binding of the antibody. By addition of EDTA (EDTA) the binding of lipopolysaccharide to T4p12 could be abolished. The resonance signal returns to its baseline. A second flow through chamber remained untreated and served as a reference. The displayed curve shows the signal difference between the measurement chamber and the reference chamber.

For this purpose first of all T4p12 was covalently coupled to the surface of a CM-5 chip (Biacore). The carboxylic residues on the surface were activated by a mixture of EDC (N-(3-dimethylaminopropyl-)carbodiimide hydrochloride, 75 mg/ml) and NHS(N-hydroxysuccinimide, 11.5 mg/ml), and subsequently T4p12 was injected, the primary amino residues of which reacted with the activated surface. The surface of a second reference chamber remained untreated. The binding of 100 µl lipopolysaccharide (*E. coli* O55:B5, 0.1 mg/ml) to T4p12 could be monitored by the increase of the resonance signal (see FIG. 6). Even after the end of the injection the resonance signal remained on its level thereby indicating a stable binding. Subsequent injections of an anti lipid A antibody (2 µg/ml, polyclonal antibody against goat lipid A from Accurate Chemical & Scientific Corporation, product number YVS6921) also indicated an increase of the resonance signal thereby a binding of the antibody, as well. The resonance signal could be reduced to its initial level by injection of EDTA (2 mM), which abrogates the binding of lipopolysaccharide to T4p12. This means, that the signal increase, induced by the injection of the antibody, was due to the binding to lipopolysaccharide.

The experiments were performed in the following buffer: 20 mM Hepes, 150 mM NaCl, 0.1 mM $CaCl_2$, pH 7.5).

Example 17

Immobilisation of Lipopolysaccharide Via T2p12 and Detection of the Binding Via an Anti Lipid a Antibody T2p12 was cloned, expressed and purified in analogy to T4p12. For the detection lipopolysaccharides of a sample solution are bound first onto a surface and subsequently these immobilised lipopolysaccharides are detected by means of a second protein binding to lipopolysaccharides. To illustrate the feasibility of this detection method, such a "sandwich" was constructed on the surface of a Biacore chip and the binding of lipopolysaccharide and a lipid A antibody was monitored by means of surface plasmon resonance measurement.

For this purpose first of all T2p12 was covalently coupled to the surface of a CM-5 chip (Biacore). The carboxyclic residues on the surface were activated by a mixture of EDC(N-(3-dimethylaminopropyl-)carbodiimide hydrochloride, 75 mg/ml) and NHS(N-hydroxysuccinimide, 11.5 mg/ml), and subsequently T2p12 was injected, the primary amino residues of which reacted with the activated surface. The surface of a second reference chamber remained untreated. The binding of 100 µl lipopolysaccharide (*E. coli* O55:B5, 0.1 mg/ml) to T2p12 could be monitored by the increase of the resonance signal. Even after the end of the injection the resonance signal remained on its level thereby indicating a stable binding. Subsequent injections of an anti lipid A antibody (2.1 µg/ml, polyclonal antibody against goat lipid A from Accurate Chemical & Scientific Corporation, product number YVS6921) also indicated an increase of the resonance signal thereby indicating the binding of the antibody, as well. The resonance signal could be lowered to its initial level by injection of EDTA (2 mM), which abrogates the binding of lipopolysaccharide to T2p12. This means, that the signal increase, induced by the injection of the antibody, was due to the binding to lipopolysaccharide. The experiments were performed in the following buffer: 20 mM Hepes, 150 mM NaCl, 0.1 mM $CaCl_2$, pH 7.5).

Example 18

Immobilisation of Lipopolysaccharide Via RB69p12 and Detection of the Binding Via an Anti Lipid a Antibody RB69p12 was cloned, expressed and purified in analogy to RB69p12. For the detection lipopolysaccharides of a sample solution are bound first onto a surface and subsequently these immobilised lipopolysaccharides are detected by means of a second protein binding to lipopolysaccharides. To illustrate the feasibility of this detection method such a "sandwich" was constructed on the surface of a Biacore chip and the binding of lipopolysaccharide and a lipid A antibody was monitored by means of surface plasmon resonance measurement.

For this purpose first of all RB69p12 was covalently coupled to the surface of a CM-5 chip (Biacore). The carboxylic residues on the surface were activated by a mixture of EDC(N-(3-dimethylaminopropyl-) carbodiimide hydrochloride, 75 mg/ml) and NHS(N-hydroxysuccinimide, 11.5 mg/ml), and subsequently RB69p12 was injected, the primary amino residues of which reacted with the activated surface. The surface of a second reference chamber remained untreated. The binding of 100 µl lipopolysaccharide (*E. coli* O55:B5, 0.1 mg/ml) to RB69p12 could be treated by the increase of the resonance signal. Even after the end of the injection the resonance signal remained on its level thereby indicating A stable binding. Subsequent injections of an anti lipid A antibody (2.1 µg/ml, polyclonal antibody against goat lipid A from Accurate Chemical & Scientific Corporation, product number YVS6921) also indicated an increase of the resonance signal thereby indicating the binding of the antibody, as well. The resonance signal could be lowered to its initial level by injection of EDTA (2 mM), which abrogates the binding of lipopolysaccharide to RB69p12. This means, that the signal increase, induced by the injection of the antibody, was due to the binding to lipopolysaccharide. The experiments were performed in the following buffer: 20 mM Hepes, 150 mM NaCl, 0.1 mM $CaCl_2$, pH 7.5).

The invention claimed is:

1. Method for detection of endotoxin, comprising the steps:
   a) incubation of a sample with a bacteriophage tail protein, and subsequently
   b) detection of endotoxin bound to bacteriophage tail proteins by means of spectroscopic methods, ELISA, chemical or enzymatic detection reaction of endotoxins or cleaved-off endotoxin components, or by means of capacitance measurements.

2. Method according to claim 1, further comprising after step a) and prior to step b) the additional step
   a') separation of the bacteriophage tail protein-endotoxin complexes from the sample.

3. Method for detection of endotoxin, the method comprising the steps of:
   a) contacting a sample containing endotoxins with a surface, subsequently
   b) incubating of bacteriophage tail proteins with the endotoxin immobilised on the surface, and
   c) detection of bacteriophage tail proteins by means of spectroscopic methods, ELISA, chemical or enzymatic detection reaction of endotoxins or cleaved-off endotoxin components, or by means of capacitance measurements.

4. Method according to claim 3 further comprising after step b) and before step c) an additional step
   b') separation of said bound bacteriophage tail proteins from endotoxin.

5. Method according to any one of the preceding claims, wherein the bacteriophage tail protein is a protein of the short bacteriophage tail fiber or a coat protein of bacteriophages without tail.

6. Method according to claim 5, wherein the protein of the short bacteriophage tail fiber is selected from K3, T2, T4, Ox2, RB32-33, AR1, PP01 and RB69.

7. Method according to claim 5 or 6, wherein the bacteriophage tail protein has a homology of at least 60% to T4p12 protein on the amino acid level.

8. Method according to any one of the preceding claims, wherein the bacteriophage tail proteins are modified.

9. Method according to any one of the preceding claims, wherein the bacteriophage tail proteins are covalently linked to enzymatically active proteins.

10. Method according to any one of the preceding claims, wherein the bacteriophage tail protein comprises a strep-tag or a his-tag.

11. Method according to claim 10, wherein the tag comprises an amino acid sequence according to SEQ ID NOS 5, 6 or 7.

12. Method according to claim 10 or 11, wherein the p12-protein of phage T4, K3, T2, Ox2, RB32-33, AR1, PP01 or RB69 is used as bacteriophage tail protein.

13. Method according to any one of the preceding claims, wherein the $Ca^{2+}$ concentration is in the incubation 0.1 µM to 10 mM and/or the $Mg^{2+}$ concentration is 0.1 µM to 10 mM.

14. Method according to any one of the preceding claims, wherein marked endotoxin is displaced from the binding with a bacteriophage tail protein and wherein the marked endotoxin is detected subsequently.

15. An endotoxin detection kit comprising a carrier coated with bacteriophage tail proteins, a container containing a reference endotoxin for measurement of a standard curve, a container with at least one further bacteriophage tail protein or an anti lipid A antibody.

16. An endotoxin detection kit comprising a carrier coated with an endotoxin binding substance, a container containing a reference endotoxin for measurement of a standard curve, and a container with at least one bacteriophage tail protein.

* * * * *

UNITED STATES PATENT AND TRADEMARK OFFICE
CERTIFICATE OF CORRECTION

PATENT NO.       : 8,551,719 B1
APPLICATION NO.  : 13/772117
DATED            : October 8, 2013
INVENTOR(S)      : Roman Meyer et al.

It is certified that error appears in the above-identified patent and that said Letters Patent is hereby corrected as shown below:

In the Claims

In claim 1, column 47, line 10, delete "Method" and insert --A method-- therefor.

In claim 2, column 47, line 18, delete "Method" and insert --A method-- therefor.

In claim 3, column 47, line 22, delete "Method" and insert --A method-- therefor.

In claim 4, column 47, line 33, delete "Method" and insert --A method-- therefor.

In claim 5, column 47, line 37, delete "Method" and insert --A method-- therefor.

In claim 5, column 47, line 37, delete "any one of the preceding claims" and insert --claim 1-- therefor.

In claim 6, column 47, line 41, delete "Method" and insert --A method-- therefor.

In claim 7, column 48, line 9, delete "Method" and insert --A method-- therefor.

In claim 7, column 48, line 9, delete "claims 5 or" and insert --claim-- therefor.

In claim 8, column 48, line 12, delete "Method" and insert --A method-- therefor.

In claim 8, column 48, line 12, delete "any one of the preceding claims" and insert --claim 1-- therefor.

In claim 9, column 48, line 14, delete "Method" and insert --A method-- therefor.

In claim 9, column 48, line 14, delete "any one of the preceding claims" and insert --claim 1-- therefor.

In claim 10, column 48, line 17, delete "Method" and insert --A method-- therefor.

Signed and Sealed this
Eighth Day of April, 2014

Michelle K. Lee
*Deputy Director of the United States Patent and Trademark Office*

CERTIFICATE OF CORRECTION (continued)
U.S. Pat. No. 8,551,719 B1

In claim 10, column 48, line 17, delete "any one of the preceding claims" and insert --claim 1-- therefor.

In claim 11, column 48, line 20, delete "Method" and insert --A method-- therefor.

In claim 12, column 48, line 23, delete "Method" and insert --A method-- therefor.

In claim 12, column 48, line 23, delete "10 or".

In claim 13, column 48, line 26, delete "Method" and insert --A method-- therefor.

In claim 13, column 48, line 26, delete "any one of the preceding claims" and insert --claim 1-- therefor.

In claim 14, column 48, line 29, delete "Method" and insert --A method-- therefor.

In claim 14, column 48, line 29, delete "any one of the preceding claims" and insert --claim 1-- therefor.

SEQUENCE LISTING

<160> NUMBER OF SEQ ID NOS: 15

<210> SEQ ID NO 1
<211> LENGTH: 78
<212> TYPE: DNA
<213> ORGANISM: Artificial Sequence
<220> FEATURE:
<223> OTHER INFORMATION: Synthetic primer

<400> SEQUENCE: 1
gaaggaacta gtcatatggc tagctggagc cacccgcagt tcgaaaaagg cgccagtaat    60
aatacatatc aacacgtt                                                 78

<210> SEQ ID NO 2
<211> LENGTH: 54
<212> TYPE: DNA
<213> ORGANISM: Artificial Sequence
<220> FEATURE:
<223> OTHER INFORMATION: Synthetic primer

<400> SEQUENCE: 2
acgcgcaaag cttgtcgacg gatcctatca ttcttttacc ttaattatgt agtt          54

<210> SEQ ID NO 3
<211> LENGTH: 78
<212> TYPE: DNA
<213> ORGANISM: Artificial Sequence
<220> FEATURE:
<223> OTHER INFORMATION: Synthetic primer

<400> SEQUENCE: 3
gaaggaacta gtcatatggc ttgttggagc cacccgcagt tcgaaaaagg cgccagtaat    60
aatacatatc aacacgtt                                                 78

<210> SEQ ID NO 4
<211> LENGTH: 78
<212> TYPE: DNA
<213> ORGANISM: Artificial Sequence
<220> FEATURE:
<223> OTHER INFORMATION: Synthetic primer

<400> SEQUENCE: 4
gaaggaacta gtcatatggc tagctggagc cacccgcagt tcgaaaaagg cgcctgtaat    60
aatacatatc aacacgtt                                                 78

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Met Ala Ser Trp Ser His Pro Gln Phe Glu Lys Gly Ala Ser Asn Asn
1               5                   10                  15

Thr Tyr Gln

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide

<400> SEQUENCE: 6

Met Ala Cys Trp Ser His Pro Gln Phe Glu Lys Gly Ala Ser Asn Asn
1               5                   10                  15

Thr Tyr Gln

<210> SEQ ID NO 7
<211> LENGTH: 19
<212> TYPE: PRT

```
<213> ORGANISM: Artificial Sequence
<220> FEATURE:
<223> OTHER INFORMATION: Synthetic peptide

<400> SEQUENCE: 7

Met Ala Ser Trp Ser His Pro Gln Phe Glu Lys Gly Ala Cys Asn Asn
1               5                   10                  15

Thr Tyr Gln

<210> SEQ ID NO 8
<211> LENGTH: 539
<212> TYPE: PRT
<213> ORGANISM: Artificial Sequence
<220> FEATURE:
<223> OTHER INFORMATION: Synthetic peptide

<400> SEQUENCE: 8

Met Ala Ser Trp Ser His Pro Gln Phe Glu Lys Gly Ala Ser Asn Asn
1               5                   10                  15

Thr Tyr Gln His Val Ser Asn Glu Ser Arg Tyr Val Lys Phe Asp Pro
                20                  25                  30

Thr Asp Thr Asn Phe Pro Pro Glu Ile Thr Asp Val Gln Ala Ala Ile
            35                  40                  45

Ala Ala Ile Ser Pro Ala Gly Val Asn Gly Val Pro Asp Ala Ser Ser
        50                  55                  60

Thr Thr Lys Gly Ile Leu Phe Leu Ala Thr Glu Gln Glu Val Ile Asp
65                  70                  75                  80

Gly Thr Asn Asn Thr Lys Ala Val Thr Pro Ala Thr Leu Ala Thr Arg
                85                  90                  95

Leu Ser Tyr Pro Asn Ala Thr Glu Ala Val Tyr Gly Leu Thr Arg Tyr
            100                 105                 110

Ser Thr Asp Asp Glu Ala Ile Ala Gly Val Asn Asn Glu Ser Ser Ile
        115                 120                 125

Thr Pro Ala Lys Phe Thr Val Ala Leu Asn Asn Val Phe Glu Thr Arg
130                 135                 140

Val Ser Thr Glu Ser Ser Asn Gly Val Ile Lys Ile Ser Ser Leu Pro
145                 150                 155                 160

Gln Ala Leu Ala Gly Ala Asp Asp Thr Ala Met Thr Pro Leu Lys
                165                 170                 175

Thr Gln Gln Leu Ala Val Lys Leu Ile Ala Gln Ile Ala Pro Ser Lys
            180                 185                 190

Asn Ala Ala Thr Glu Ser Glu Gln Gly Val Ile Gln Leu Ala Thr Val
        195                 200                 205

Ala Gln Ala Arg Gln Gly Thr Leu Arg Glu Gly Tyr Ala Ile Ser Pro
    210                 215                 220

Tyr Thr Phe Met Asn Ser Thr Ala Thr Glu Glu Tyr Lys Gly Val Ile
225                 230                 235                 240

Lys Leu Gly Thr Gln Ser Glu Val Asn Ser Asn Ala Ser Val Ala
                245                 250                 255

Val Thr Gly Ala Thr Leu Asn Gly Arg Gly Ser Thr Ser Met Arg
            260                 265                 270

Gly Val Val Lys Leu Thr Thr Thr Ala Gly Ser Gln Ser Gly Asp
        275                 280                 285

Ala Ser Ser Ala Leu Ala Trp Asn Ala Asp Val Ile His Gln Arg Gly
    290                 295                 300

Gly Gln Thr Ile Asn Gly Thr Leu Arg Ile Asn Asn Thr Leu Thr Ile
305                 310                 315                 320
```

```
Ala Ser Gly Gly Ala Asn Ile Thr Gly Thr Val Asn Met Thr Gly Gly
            325                 330                 335

Tyr Ile Gln Gly Lys Arg Val Val Thr Gln Asn Glu Ile Asp Arg Thr
            340                 345                 350

Ile Pro Val Gly Ala Ile Met Met Trp Ala Ala Asp Ser Leu Pro Ser
            355                 360                 365

Asp Ala Trp Arg Phe Cys His Gly Gly Thr Val Ser Ala Ser Asp Cys
        370                 375                 380

Pro Leu Tyr Ala Ser Arg Ile Gly Thr Arg Tyr Gly Ser Ser Ser
385                 390                 395                 400

Asn Pro Gly Leu Pro Asp Met Arg Gly Leu Phe Val Arg Gly Ser Gly
            405                 410                 415

Arg Gly Ser His Leu Thr Asn Pro Asn Val Asn Gly Asn Asp Gln Phe
            420                 425                 430

Gly Lys Pro Arg Leu Gly Val Gly Cys Thr Gly Gly Tyr Val Gly Glu
        435                 440                 445

Val Gln Lys Gln Gln Met Ser Tyr His Lys His Ala Gly Gly Phe Gly
450                 455                 460

Glu Tyr Asp Asp Ser Gly Ala Phe Gly Asn Thr Arg Arg Ser Asn Phe
465                 470                 475                 480

Val Gly Thr Arg Lys Gly Leu Asp Trp Asp Asn Arg Ser Tyr Phe Thr
            485                 490                 495

Asn Asp Gly Tyr Glu Ile Asp Pro Ala Ser Gln Arg Asn Ser Arg Tyr
        500                 505                 510

Thr Leu Asn Arg Pro Glu Leu Ile Gly Asn Glu Thr Arg Pro Trp Asn
            515                 520                 525

Ile Ser Leu Asn Tyr Ile Ile Lys Val Lys Glu
            530                 535

<210> SEQ ID NO 9
<211> LENGTH: 527
<212> TYPE: PRT
<213> ORGANISM: Artificial Sequence
<220> FEATURE:
<223> OTHER INFORMATION: Synthetic peptide

<400> SEQUENCE: 9

Met Ser Asn Asn Thr Tyr Gln His Val Ser Asn Glu Ser Arg Tyr Val
1               5                   10                  15

Lys Phe Asp Pro Thr Asp Thr Asn Phe Pro Pro Glu Ile Thr Asp Val
            20                  25                  30

Gln Ala Ala Ile Ala Ala Ile Ser Pro Ala Gly Val Asn Gly Val Pro
        35                  40                  45

Asp Ala Ser Ser Thr Thr Lys Gly Ile Leu Phe Leu Ala Thr Glu Gln
50                  55                  60

Glu Val Ile Asp Gly Thr Asn Thr Lys Ala Val Thr Pro Ala Thr
65                  70                  75                  80

Leu Ala Thr Arg Leu Ser Tyr Pro Asn Ala Thr Glu Ala Val Tyr Gly
            85                  90                  95

Leu Thr Arg Tyr Ser Thr Asp Asp Glu Ala Ile Ala Gly Val Asn Asn
            100                 105                 110

Glu Ser Ser Ile Thr Pro Ala Lys Phe Thr Val Ala Leu Asn Asn Val
        115                 120                 125

Phe Glu Thr Arg Val Ser Thr Glu Ser Ser Asn Gly Val Ile Lys Ile
    130                 135                 140
```

Ser Ser Leu Pro Gln Ala Leu Ala Gly Ala Asp Asp Thr Thr Ala Met
145                 150                 155                 160

Thr Pro Leu Lys Thr Gln Gln Leu Ala Val Lys Leu Ile Ala Gln Ile
            165                 170                 175

Ala Pro Ser Lys Asn Ala Ala Thr Glu Ser Glu Gln Gly Val Ile Gln
            180                 185                 190

Leu Ala Thr Val Ala Gln Ala Arg Gln Gly Thr Leu Arg Glu Gly Tyr
        195                 200                 205

Ala Ile Ser Pro Tyr Thr Phe Met Asn Ser Thr Ala Thr Glu Glu Tyr
    210                 215                 220

Lys Gly Val Ile Lys Leu Gly Thr Gln Ser Glu Val Asn Ser Asn Asn
225                 230                 235                 240

Ala Ser Val Ala Val Thr Gly Ala Thr Leu Asn Gly Arg Gly Ser Thr
            245                 250                 255

Thr Ser Met Arg Gly Val Val Lys Leu Thr Thr Thr Ala Gly Ser Gln
            260                 265                 270

Ser Gly Gly Asp Ala Ser Ser Ala Leu Ala Trp Asn Ala Asp Val Ile
        275                 280                 285

His Gln Arg Gly Gly Gln Thr Ile Asn Gly Thr Leu Arg Ile Asn Asn
    290                 295                 300

Thr Leu Thr Ile Ala Ser Gly Ala Asn Ile Thr Gly Thr Val Asn
305                 310                 315                 320

Met Thr Gly Gly Tyr Ile Gln Gly Lys Arg Val Val Thr Gln Asn Glu
            325                 330                 335

Ile Asp Arg Thr Ile Pro Val Gly Ala Ile Met Met Trp Ala Ala Asp
        340                 345                 350

Ser Leu Pro Ser Asp Ala Trp Arg Phe Cys His Gly Thr Val Ser
    355                 360                 365

Ala Ser Asp Cys Pro Leu Tyr Ala Ser Arg Ile Gly Thr Arg Tyr Gly
    370                 375                 380

Gly Thr Ser Ser Asn Pro Gly Leu Pro Asp Met Arg Gly Leu Phe Val
385                 390                 395                 400

Arg Gly Ser Gly Arg Gly Ser His Leu Thr Asn Pro Asn Val Asn Gly
            405                 410                 415

Asn Asp Gln Phe Gly Lys Pro Arg Leu Gly Val Gly Cys Thr Gly Gly
            420                 425                 430

Tyr Val Gly Glu Val Gln Lys Gln Gln Met Ser Tyr His Lys His Ala
        435                 440                 445

Gly Gly Phe Gly Glu Tyr Asp Asp Ser Gly Ala Phe Gly Asn Thr Arg
    450                 455                 460

Arg Ser Asn Phe Val Gly Thr Arg Lys Gly Leu Asp Trp Asp Asn Arg
465                 470                 475                 480

Ser Tyr Phe Thr Asn Asp Gly Tyr Glu Ile Asp Pro Ala Ser Gln Arg
            485                 490                 495

Asn Ser Arg Tyr Thr Leu Asn Arg Pro Glu Leu Ile Gly Asn Glu Thr
            500                 505                 510

Arg Pro Trp Asn Ile Ser Leu Asn Tyr Ile Ile Lys Val Lys Glu
        515                 520                 525

<210> SEQ ID NO 10
<211> LENGTH: 527
<212> TYPE: PRT
<213> ORGANISM: Artificial Sequence
<220> FEATURE:
<223> OTHER INFORMATION: Synthetic peptide

<400> SEQUENCE: 10

```
Met Ser Asn Asn Thr Tyr Gln His Val Ser Asn Glu Ser Arg Tyr Val
1               5                   10                  15

Lys Phe Asp Pro Thr Asp Thr Asn Phe Pro Pro Glu Ile Thr Asp Val
            20                  25                  30

His Ala Ala Ile Ala Ala Ile Ser Pro Ala Gly Val Asn Gly Val Pro
        35                  40                  45

Asp Ala Ser Ser Thr Thr Lys Gly Ile Leu Phe Ile Pro Thr Glu Gln
    50                  55                  60

Glu Val Ile Asp Gly Thr Asn Asn Thr Lys Ala Val Thr Pro Ala Thr
65                  70                  75                  80

Leu Ala Thr Arg Leu Ser Tyr Pro Asn Ala Thr Glu Thr Val Tyr Gly
                85                  90                  95

Leu Thr Arg Tyr Ser Thr Asn Asp Glu Ala Ile Ala Gly Val Asn Asn
            100                 105                 110

Glu Ser Ser Ile Thr Pro Ala Lys Phe Thr Val Ala Leu Asn Asn Ala
        115                 120                 125

Phe Glu Thr Arg Val Ser Thr Glu Ser Ser Asn Gly Val Ile Lys Ile
    130                 135                 140

Ser Ser Leu Pro Gln Ala Leu Ala Gly Ala Asp Asp Thr Thr Ala Met
145                 150                 155                 160

Thr Pro Leu Lys Thr Gln Gln Leu Ala Ile Lys Leu Ile Ala Gln Ile
                165                 170                 175

Ala Pro Ser Glu Thr Thr Ala Thr Glu Ser Asp Gln Gly Val Val Gln
            180                 185                 190

Leu Ala Thr Val Ala Gln Val Arg Gln Gly Thr Leu Arg Glu Gly Tyr
        195                 200                 205

Ala Ile Ser Pro Tyr Thr Phe Met Asn Ser Ser Thr Glu Glu Tyr
    210                 215                 220

Lys Gly Val Ile Lys Leu Gly Thr Gln Ser Glu Val Asn Ser Asn Asn
225                 230                 235                 240

Ala Ser Val Ala Val Thr Gly Ala Thr Leu Asn Gly Arg Gly Ser Thr
                245                 250                 255

Thr Ser Met Arg Gly Val Val Lys Leu Thr Thr Ala Gly Ser Gln
            260                 265                 270

Ser Gly Gly Asp Ala Ser Ser Ala Leu Ala Trp Asn Ala Asp Val Ile
        275                 280                 285

Gln Gln Arg Gly Gly Gln Ile Ile Tyr Gly Thr Leu Arg Ile Glu Asp
    290                 295                 300

Thr Phe Thr Ile Ala Asn Gly Ala Asn Ile Thr Gly Thr Val Arg
305                 310                 315                 320

Met Thr Gly Gly Tyr Ile Gln Gly Asn Arg Ile Val Thr Gln Asn Glu
                325                 330                 335

Ile Asp Arg Thr Ile Pro Val Gly Ala Ile Met Met Trp Ala Ala Asp
            340                 345                 350

Ser Leu Pro Ser Asp Ala Trp Arg Phe Cys His Gly Thr Val Ser
        355                 360                 365

Ala Ser Asp Cys Pro Leu Tyr Ala Ser Arg Ile Gly Thr Arg Tyr Gly
    370                 375                 380

Gly Asn Pro Ser Asn Pro Gly Leu Pro Asp Met Arg Gly Leu Phe Val
385                 390                 395                 400

Arg Gly Ser Gly Arg Gly Ser His Leu Thr Asn Pro Asn Val Asn Gly
                405                 410                 415
```

```
Asn Asp Gln Phe Gly Lys Pro Arg Leu Gly Val Gly Cys Thr Gly Gly
            420                 425                 430

Tyr Val Gly Glu Val Gln Ile Gln Gln Met Ser Tyr His Lys His Ala
            435                 440                 445

Gly Gly Phe Gly Glu His Asp Asp Leu Gly Ala Phe Gly Asn Thr Arg
            450                 455                 460

Arg Ser Asn Phe Val Gly Thr Arg Lys Gly Leu Asp Trp Asp Asn Arg
465                 470                 475                 480

Ser Tyr Phe Thr Asn Asp Gly Tyr Glu Ile Asp Pro Glu Ser Gln Arg
                    485                 490                 495

Asn Ser Lys Tyr Thr Leu Asn Arg Pro Glu Leu Ile Gly Asn Glu Thr
            500                 505                 510

Arg Pro Trp Asn Ile Ser Leu Asn Tyr Ile Ile Lys Val Lys Glu
            515                 520                 525

<210> SEQ ID NO 11
<211> LENGTH: 518
<212> TYPE: PRT
<213> ORGANISM: Artificial Sequence
<220> FEATURE:
<223> OTHER INFORMATION: Synthetic peptide

<400> SEQUENCE: 11

Met Ser Asn Asn Thr Tyr Gln His Val Ser Asn Glu Ser Lys Tyr Val
1               5                   10                  15

Lys Phe Asp Pro Val Gly Ser Asn Phe Pro Asp Thr Val Thr Thr Val
                20                  25                  30

Gln Ser Ala Leu Ser Lys Ile Ser Asn Ile Gly Val Asn Gly Ile Pro
            35                  40                  45

Asp Ala Ser Met Glu Val Lys Gly Ile Ala Met Ile Ala Ser Glu Gln
        50                  55                  60

Glu Val Leu Asp Gly Thr Asn Asn Ser Lys Ile Val Thr Pro Ala Thr
65                  70                  75                  80

Leu Ala Thr Arg Leu Leu Tyr Pro Asn Ala Thr Glu Thr Lys Tyr Gly
                85                  90                  95

Leu Thr Arg Tyr Ser Thr Asn Glu Glu Thr Leu Glu Gly Ser Asp Asn
            100                 105                 110

Asn Ser Ser Ile Thr Pro Gln Lys Leu Lys Tyr His Thr Asp Asp Val
        115                 120                 125

Phe Gln Asn Arg Tyr Ser Ser Glu Ser Ser Asn Gly Val Ile Lys Ile
130                 135                 140

Ser Ser Thr Pro Ala Ala Leu Ala Gly Val Asp Asp Thr Thr Ala Met
145                 150                 155                 160

Thr Pro Leu Lys Thr Gln Lys Leu Ala Ile Lys Leu Ile Ser Gln Ile
                165                 170                 175

Ala Pro Ser Glu Asp Thr Ala Ser Glu Ser Val Arg Gly Val Val Gln
            180                 185                 190

Leu Ser Thr Val Ala Gln Thr Arg Gln Gly Thr Leu Arg Glu Gly Tyr
        195                 200                 205

Ala Ile Ser Pro Tyr Thr Phe Met Asn Ser Val Ala Thr Gln Glu Tyr
    210                 215                 220

Lys Gly Val Ile Arg Leu Gly Thr Gln Ser Glu Ile Asn Ser Asn Leu
225                 230                 235                 240

Gly Asp Val Ala Val Thr Gly Glu Thr Leu Asn Gly Arg Gly Ala Thr
                245                 250                 255

Gly Ser Met Arg Gly Val Val Lys Leu Thr Thr Gln Ala Gly Ile Ala
```

```
                    260                 265                 270
Pro Glu Gly Asp Ser Ser Gly Ala Leu Ala Trp Asn Ala Asp Val Ile
                275                 280                 285

Asn Thr Arg Gly Gly Gln Thr Ile Asn Gly Ser Leu Asn Leu Asp His
            290                 295                 300

Leu Thr Ala Asn Gly Ile Trp Ser Arg Gly Gly Met Trp Lys Asn Gly
305                 310                 315                 320

Asp Gln Pro Val Ala Thr Glu Arg Tyr Ala Ser Glu Arg Val Pro Val
                325                 330                 335

Gly Thr Ile Met Met Phe Ala Gly Asp Ser Ala Pro Pro Gly Trp Ile
            340                 345                 350

Met Cys His Gly Gly Thr Val Ser Gly Asp Gln Tyr Pro Asp Tyr Arg
            355                 360                 365

Asn Thr Val Gly Thr Arg Phe Gly Gly Asp Trp Asn Asn Pro Gly Ile
            370                 375                 380

Pro Asp Met Arg Gly Leu Phe Val Arg Gly Ala Gly Thr Gly Gly His
385                 390                 395                 400

Ile Leu Asn Gln Arg Gly Gln Asp Gly Tyr Gly Lys Asp Arg Leu Gly
                405                 410                 415

Val Gly Cys Asp Gly Met His Val Gly Val Gln Ala Gln Gln Ile
            420                 425                 430

Ser Tyr His Lys His Ala Gly Ala Trp Gly Glu Asn Gly Asn Asn Arg
            435                 440                 445

Gly Tyr Ala Pro Phe Gly Ala Ser Asn Gly Ser Gly Tyr Leu Gly Asn
            450                 455                 460

Gly Arg Ser Ala Asp Trp Asp Asn His Leu Phe Phe Thr Asn Asp Gly
465                 470                 475                 480

Phe Glu Met Gly Gly Pro Arg Asp Ser Phe Gly Thr Leu Asn Arg Glu
                485                 490                 495

Gly Leu Ile Gly Tyr Glu Thr Arg Pro Trp Asn Ile Ser Leu Asn Tyr
                500                 505                 510

Ile Ile Lys Ile His Tyr
            515

<210> SEQ ID NO 12
<211> LENGTH: 516
<212> TYPE: PRT
<213> ORGANISM: Artificial Sequence
<220> FEATURE:
<223> OTHER INFORMATION: Synthetic peptide

<400> SEQUENCE: 12

Met Ser Asn Asn Thr Tyr Gln His Val Ser Asn Glu Ser Val Tyr Val
1               5                   10                  15

Glu Phe Asp Pro Thr Gly Ser Asn Phe Asp Ser Ser Ile Thr Asn Val
                20                  25                  30

Gln Ala Ala Leu Ala Ser Ile Ser Ala Tyr Gly Val Lys Gly Val Pro
            35                  40                  45

Asp Ala Ser Glu Ala Glu Lys Gly Val Ile Gln Leu Ala Thr Glu Gln
        50                  55                  60

Glu Val Leu Asp Gly Phe Asn Ser Thr Lys Ala Val Thr Pro Ala Thr
65                  70                  75                  80

Leu Asn Ala Arg Leu Gln Tyr Pro Asn Ala Ser Glu Thr Gln Tyr Gly
                85                  90                  95

Val Thr Lys Tyr Ala Thr Gln Glu Glu Ala Ile Ala Gly Thr Leu Asp
            100                 105                 110
```

-continued

```
Thr Val Ser Ile Thr Pro Leu Lys Leu Asn Gln Thr Ile Asp Asn Thr
        115                 120                 125

Phe Ser Thr Arg Tyr Ser Thr Glu Thr Thr Asn Gly Val Ile Lys Ile
    130                 135                 140

Ala Thr Gln Thr Ala Ala Leu Ala Gly Ser Asp Asp Thr Thr Ala Met
145                 150                 155                 160

Thr Pro Leu Lys Thr Gln Gln Leu Ala Ile Lys Leu Ile Ser Gln Ile
                165                 170                 175

Ala Pro Asn Asn Asp Pro Ala Ser Glu Ser Ile Thr Gly Val Val Arg
            180                 185                 190

Leu Ala Thr Val Ala Gln Thr Arg Gln Gly Thr Leu Arg Glu Gly Tyr
        195                 200                 205

Ala Ile Ser Pro Tyr Thr Phe Met Asn Ser Val Ala Thr Gln Glu Tyr
    210                 215                 220

Lys Gly Val Ile Arg Leu Gly Thr Gln Ala Glu Ile Asn Ser Asn Leu
225                 230                 235                 240

Gly Asp Val Ala Val Thr Gly Glu Thr Leu Asn Gly Arg Gly Ala Thr
                245                 250                 255

Gly Ser Met Arg Gly Val Val Lys Leu Thr Thr Gln Ala Gly Val Ala
            260                 265                 270

Pro Glu Gly Asp Ser Ser Gly Ala Leu Ala Trp Asn Ala Asp Val Ile
        275                 280                 285

Asn Thr Arg Gly Gly Gln Thr Ile Asn Gly Ser Leu Asn Leu Asp His
    290                 295                 300

Leu Thr Ala Asn Gly Ile Trp Ser Arg Gly Gly Met Trp Lys Asn Gly
305                 310                 315                 320

Asp Gln Pro Val Ala Thr Glu Arg Tyr Ala Ser Glu Arg Val Pro Val
                325                 330                 335

Gly Thr Ile Gln Met Phe Ala Gly Asp Ser Ala Pro Pro Gly Trp Val
            340                 345                 350

Leu Cys His Gly Gly Thr Ile Ser Gly Asp Gln Phe Pro Asp Tyr Arg
        355                 360                 365

Asn Val Val Gly Thr Arg Phe Gly Gly Asp Trp Asn Asn Pro Gly Ile
    370                 375                 380

Pro Asp Met Arg Gly Leu Phe Val Arg Gly Ala Gly Thr Gly Ser His
385                 390                 395                 400

Ile Leu Asn Asn Arg Gly Gln Asp Gly Tyr Gly Lys Asp Arg Leu Gly
                405                 410                 415

Val Gly Cys Asp Gly Met His Val Gly Gly Val Gln Ala Gln Gln Met
            420                 425                 430

Ser Tyr His Lys His Ala Gly Gly Trp Gly Glu Phe Gln Arg His Glu
        435                 440                 445

Ala Pro Phe Gly Ala Ser Val Tyr Gln Gly Tyr Leu Gly Thr Arg Lys
    450                 455                 460

Tyr Ser Asp Trp Asp Asn Ala Ser Tyr Phe Thr Asn Asp Gly Phe Glu
465                 470                 475                 480

Leu Gly Gly His Arg Asp Ala Thr Gly Thr Leu Asn Arg Glu Gly Leu
                485                 490                 495

Ile Gly Tyr Glu Thr Arg Pro Trp Asn Ile Ser Leu Asn Tyr Ile Ile
            500                 505                 510

Lys Val His Tyr
        515
```

```
<210> SEQ ID NO 13
<211> LENGTH: 516
<212> TYPE: PRT
<213> ORGANISM: Artificial Sequence
<220> FEATURE:
<223> OTHER INFORMATION: Synthetic peptide

<400> SEQUENCE: 13

Met Ser Asn Asn Thr Tyr Gln His Val Ser Asn Glu Ser Lys Tyr Val
1               5                   10                  15

Lys Phe Asp Pro Thr Gly Ser Asn Phe Pro Asp Thr Val Thr Thr Val
            20                  25                  30

Gln Ser Ala Leu Ser Lys Ile Ser Asn Ile Gly Val Asn Gly Ile Pro
        35                  40                  45

Asp Ala Thr Met Glu Val Lys Gly Ile Ala Met Ile Ala Ser Glu Gln
    50                  55                  60

Glu Val Leu Asp Gly Thr Asn Asn Ser Lys Ile Val Thr Pro Ala Thr
65                  70                  75                  80

Leu Ala Thr Arg Leu Leu Tyr Pro Asn Ala Thr Glu Thr Lys Tyr Gly
                85                  90                  95

Leu Thr Arg Tyr Ser Thr Asn Glu Glu Thr Leu Glu Gly Ser Asp Asn
            100                 105                 110

Asn Ser Ser Ile Thr Pro Gln Lys Leu Lys Tyr His Thr Asp Asp Val
        115                 120                 125

Phe Gln Asn Arg Tyr Ser Ser Glu Ser Ser Asn Gly Val Ile Lys Ile
    130                 135                 140

Ser Ser Thr Pro Ala Ala Leu Ala Gly Val Asp Asp Thr Thr Ala Met
145                 150                 155                 160

Thr Pro Leu Lys Thr Gln Lys Leu Ala Ile Lys Leu Ile Ser Gln Ile
                165                 170                 175

Ala Pro Ser Glu Asp Thr Ala Ser Glu Ser Val Arg Gly Val Val Gln
            180                 185                 190

Leu Ser Thr Val Ala Gln Thr Arg Gln Gly Thr Leu Arg Glu Gly Tyr
        195                 200                 205

Ala Ile Ser Pro Tyr Thr Phe Met Asn Ser Val Ala Thr Gln Glu Tyr
    210                 215                 220

Lys Gly Val Ile Arg Leu Gly Thr Gln Ser Glu Ile Asn Ser Asn Leu
225                 230                 235                 240

Gly Asp Val Ala Val Thr Gly Gly Thr Leu Asn Gly Arg Gly Ala Thr
                245                 250                 255

Gly Ser Met Arg Gly Val Val Lys Leu Thr Thr Gln Ala Gly Ile Ala
            260                 265                 270

Pro Glu Gly Asp Ser Ser Gly Ala Leu Ala Trp Asn Ala Asp Val Ile
        275                 280                 285

Asn Thr Arg Gly Gly Gln Thr Ile Asn Gly Ser Leu Asn Leu Asp His
    290                 295                 300

Leu Thr Ala Asn Gly Ile Trp Ser Arg Gly Met Trp Lys Asn Gly
305                 310                 315                 320

Asp Gln Pro Val Ala Thr Glu Arg Tyr Ala Ser Glu Arg Val Pro Val
                325                 330                 335

Gly Thr Ile Met Met Phe Ala Gly Asp Ser Ala Pro Gly Trp Ile
            340                 345                 350

Met Cys His Gly Gly Thr Val Ser Gly Asp Gln Tyr Pro Asp Tyr Arg
        355                 360                 365

Asn Thr Val Gly Thr Arg Phe Gly Gly Asp Trp Asn Asn Pro Gly Ile
    370                 375                 380
```

```
Pro Asp Met Arg Gly Leu Phe Val Arg Gly Ala Gly Thr Gly His
385                 390                 395                 400

Ile Leu Asn Gln Arg Gly Gln Asp Gly Tyr Gly Lys Asp Arg Leu Gly
                405                 410                 415

Val Gly Cys Asp Gly Met His Val Gly Val Gln Ala Gln Gln Met
            420                 425                 430

Ser Tyr His Lys His Ala Gly Gly Trp Gly Glu Tyr Asn Arg Ser Glu
        435                 440                 445

Gly Pro Phe Gly Ala Ser Val Tyr Gln Gly Tyr Leu Gly Thr Arg Lys
        450                 455                 460

Tyr Ser Asp Trp Asp Asn Ala Ser Tyr Phe Thr Asn Asp Gly Phe Glu
465                 470                 475                 480

Leu Gly Gly Pro Arg Asp Ala Leu Gly Thr Leu Asn Arg Glu Gly Leu
                485                 490                 495

Ile Gly Tyr Glu Thr Arg Pro Trp Asn Ile Ser Leu Asn Tyr Ile Ile
            500                 505                 510

Lys Ile His Tyr
        515

<210> SEQ ID NO 14
<211> LENGTH: 527
<212> TYPE: PRT
<213> ORGANISM: Artificial Sequence
<220> FEATURE:
<223> OTHER INFORMATION: Synthetic peptide

<400> SEQUENCE: 14

Met Ser Asn Asn Thr Tyr Gln His Val Ser Asn Glu Ser Arg Tyr Val
1               5                   10                  15

Lys Phe Asp Pro Thr Asp Thr Asn Phe Pro Pro Glu Ile Thr Asp Val
                20                  25                  30

Gln Ala Ala Ile Ala Ala Ile Ser Pro Ala Gly Val Asn Gly Val Pro
            35                  40                  45

Asp Ala Ser Ser Thr Thr Lys Gly Ile Leu Phe Leu Ala Thr Glu Gln
    50                  55                  60

Glu Val Ile Asp Gly Thr Asn Asn Thr Lys Ala Val Thr Pro Ala Thr
65                  70                  75                  80

Leu Ala Thr Arg Leu Ser Tyr Pro Asn Ala Thr Glu Thr Val Tyr Gly
                85                  90                  95

Leu Thr Arg Tyr Ser Thr Asn Asp Glu Ala Ile Ala Gly Val Asn Asn
            100                 105                 110

Glu Ser Ser Ile Thr Pro Ala Lys Phe Thr Val Ala Leu Asn Asn Ala
        115                 120                 125

Phe Glu Thr Arg Val Ser Thr Glu Ser Ser Asn Gly Val Ile Lys Ile
    130                 135                 140

Ser Ser Leu Pro Gln Ala Leu Ala Gly Ala Asp Asp Thr Thr Ala Met
145                 150                 155                 160

Thr Pro Leu Lys Thr Gln Gln Leu Ala Ile Lys Leu Ile Ala Gln Ile
                165                 170                 175

Ala Pro Ser Glu Thr Thr Ala Thr Glu Ser Asp Gln Gly Val Val Gln
            180                 185                 190

Leu Ala Thr Val Ala Gln Val Arg Gln Gly Thr Leu Arg Glu Gly Tyr
        195                 200                 205

Ala Ile Ser Pro Tyr Thr Phe Met Asn Ser Ser Ala Thr Glu Glu Tyr
    210                 215                 220
```

```
Lys Gly Val Ile Lys Leu Gly Thr Gln Ser Glu Val Asn Ser Asn Asn
225                 230                 235                 240

Ala Ser Val Ala Val Thr Gly Ala Thr Leu Asn Gly Arg Gly Ser Thr
            245                 250                 255

Thr Ser Met Arg Gly Val Val Arg Leu Thr Thr Thr Ala Gly Ser Gln
        260                 265                 270

Ser Gly Gly Asp Ala Ser Ser Ala Leu Ala Trp Asn Ala Asp Val Ile
    275                 280                 285

His Gln Arg Gly Gly Gln Thr Ile Asn Gly Thr Leu Arg Ile Asn Asn
290                 295                 300

Thr Leu Thr Ile Ala Ser Gly Gly Ala Asn Ile Thr Gly Thr Val Asn
305                 310                 315                 320

Met Thr Gly Gly Tyr Ile Gln Gly Lys Arg Val Val Thr Gln Asn Glu
            325                 330                 335

Ile Asp Arg Thr Ile Pro Val Gly Ala Ile Met Met Trp Ala Ala Asp
        340                 345                 350

Ser Leu Pro Ser Asp Ala Trp Arg Phe Cys His Gly Gly Thr Val Ser
    355                 360                 365

Ala Ser Asp Cys Pro Leu Tyr Ala Ser Arg Ile Gly Thr Arg Tyr Gly
370                 375                 380

Gly Ser Ser Asn Pro Gly Leu Pro Asp Met Arg Gly Leu Phe Val
385                 390                 395                 400

Arg Gly Ser Gly Arg Gly Ser His Leu Thr Asn Pro Asn Val Asn Gly
            405                 410                 415

Asn Asp Gln Phe Gly Lys Pro Arg Leu Gly Val Gly Cys Thr Gly Gly
        420                 425                 430

Tyr Val Gly Glu Val Gln Lys Gln Gln Met Ser Tyr His Lys His Ala
    435                 440                 445

Gly Gly Phe Gly Glu Trp Asp Asp Ser Gly Ala Phe Gly Asn Thr Arg
450                 455                 460

Arg Ser Asn Phe Val Gly Thr Arg Lys Gly Leu Asp Trp Asp Asn Arg
465                 470                 475                 480

Ser Tyr Phe Thr Asn Asp Gly Tyr Glu Ile Asp Pro Ala Ser Gln Arg
            485                 490                 495

Asn Ser Arg Tyr Thr Leu Asn Arg Pro Glu Leu Ile Gly Asn Glu Thr
        500                 505                 510

Arg Pro Trp Asn Ile Ser Leu Asn Tyr Ile Ile Lys Val Lys Glu
    515                 520                 525

<210> SEQ ID NO 15
<211> LENGTH: 516
<212> TYPE: PRT
<213> ORGANISM: Artificial Sequence
<220> FEATURE:
<223> OTHER INFORMATION: Synthetic peptide

<400> SEQUENCE: 15

Met Ser Asn Asn Thr Tyr Gln His Val Ser Asn Glu Ser Lys Tyr Val
1               5                   10                  15

Lys Phe Asp Pro Val Gly Ser Asn Phe Pro Asp Thr Val Thr Thr Val
            20                  25                  30

Gln Ser Ala Leu Ser Lys Ile Ser Asn Ile Gly Val Asn Gly Ile Pro
        35                  40                  45

Asp Ala Thr Met Glu Val Lys Gly Ile Ala Met Ile Ala Ser Glu Gln
    50                  55                  60

Glu Val Leu Asp Gly Thr Asn Asn Ser Lys Ile Val Thr Pro Ala Thr
```

```
                65                  70                  75                  80
Leu Ala Thr Arg Leu Leu Tyr Pro Asn Ala Thr Glu Thr Lys Tyr Gly
                    85                  90                  95

Leu Thr Arg Tyr Ser Thr Asn Glu Glu Thr Leu Glu Gly Ser Asp Asn
                    100                 105                 110

Asn Ser Ser Ile Thr Pro Gln Lys Leu Lys Tyr His Thr Asp Asp Val
                    115                 120                 125

Phe Gln Asn Arg Tyr Ser Ser Glu Ser Ser Asn Gly Val Ile Lys Ile
        130                 135                 140

Ser Ser Thr Pro Ala Ala Leu Ala Gly Val Asp Asp Thr Thr Ala Met
145                 150                 155                 160

Thr Pro Leu Lys Thr Gln Lys Leu Ala Ile Lys Leu Ile Ser Gln Ile
                    165                 170                 175

Ala Pro Ser Glu Asp Thr Ala Ser Glu Ser Val Arg Gly Val Val Gln
                    180                 185                 190

Leu Ser Thr Val Ala Gln Thr Arg Gln Gly Thr Leu Arg Glu Gly Tyr
                    195                 200                 205

Ala Ile Ser Pro Tyr Thr Phe Met Asn Ser Val Ala Thr Gln Glu Tyr
        210                 215                 220

Lys Gly Val Ile Arg Leu Gly Thr Gln Ser Glu Ile Asn Ser Asn Leu
225                 230                 235                 240

Gly Asp Val Ala Val Thr Gly Glu Thr Leu Asn Gly Arg Gly Ala Thr
                    245                 250                 255

Ser Ser Met Arg Gly Val Val Lys Leu Thr Thr Gln Ala Gly Ile Ala
                    260                 265                 270

Pro Glu Gly Asp Gly Ser Gly Ala Leu Ala Trp Asn Ala Asp Val Ile
                    275                 280                 285

Asn Thr Arg Gly Gly Gln Thr Ile Asn Gly Ser Leu Asn Leu Asp His
        290                 295                 300

Leu Thr Ala Asn Gly Ile Trp Ser Arg Gly Gly Met Trp Lys Asn Gly
305                 310                 315                 320

Asp Gln Pro Val Ala Thr Glu Arg Tyr Ala Ser Glu Arg Val Pro Val
                    325                 330                 335

Gly Thr Ile Met Met Phe Ala Gly Asp Ser Ala Pro Pro Gly Trp Ile
                    340                 345                 350

Met Cys His Gly Gly Thr Val Ser Gly Asp Gln Tyr Pro Asp Tyr Arg
                    355                 360                 365

Asn Thr Val Gly Ala Arg Phe Gly Gly Asp Trp Asn Asn Pro Gly Ile
        370                 375                 380

Pro Asp Met Arg Gly Leu Phe Val Arg Gly Ala Gly Thr Gly Gly His
385                 390                 395                 400

Ile Leu Asn Gln Arg Gly Gln Asp Gly Tyr Gly Lys Asp Arg Leu Gly
                    405                 410                 415

Val Gly Cys Asp Gly Met His Val Gly Gly Val Gln Ala Gln Gln Met
                    420                 425                 430

Ser Tyr His Lys His Ala Gly Gly Trp Gly Glu Tyr Gln Arg His Glu
                    435                 440                 445

Ala Pro Phe Gly Ala Ser Val Tyr Gln Gly Tyr Leu Gly Thr Arg Lys
        450                 455                 460

Tyr Ser Asp Trp Asp Asn Ala Ser Tyr Phe Thr Asn Asp Gly Phe Glu
465                 470                 475                 480

Leu Gly Gly Pro Arg Asp Ala Leu Gly Thr Leu Asn Arg Glu Gly Leu
                    485                 490                 495
```

```
Ile Gly Tyr Glu Thr Arg Pro Trp Asn Ile Ser Leu Asn Tyr Ile Ile
            500                 505                 510

Lys Ile His Tyr
        515
```